US010149921B2

(12) United States Patent
Jin et al.

(10) Patent No.: US 10,149,921 B2
(45) Date of Patent: *Dec. 11, 2018

(54) IMPLANTS HAVING TANTALUM COATED NANOSTRUCTURES

(71) Applicant: THE REGENTS OF THE UNIVERSITY OF CALIFORNIA, Oakland, CA (US)

(72) Inventors: Sungho Jin, San Diego, CA (US); Christine Frandsen, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/814,896

(22) PCT Filed: Feb. 7, 2013

(86) PCT No.: PCT/US2013/025090
§ 371 (c)(1),
(2) Date: Apr. 5, 2013

(87) PCT Pub. No.: WO2013/119772
PCT Pub. Date: Aug. 15, 2013

(65) Prior Publication Data
US 2014/0086962 A1 Mar. 27, 2014

Related U.S. Application Data

(60) Provisional application No. 61/596,143, filed on Feb. 7, 2012.

(51) Int. Cl.
*A61L 27/30* (2006.01)
*C12M 1/12* (2006.01)
*B82Y 30/00* (2011.01)
*A61L 27/38* (2006.01)
*A61F 2/30* (2006.01)
*B22F 1/00* (2006.01)
*B22F 1/02* (2006.01)
*A61L 27/04* (2006.01)
*A61L 31/02* (2006.01)
*A61L 31/08* (2006.01)

(52) U.S. Cl.
CPC ........ *A61L 27/306* (2013.01); *A61F 2/30767* (2013.01); *A61L 27/047* (2013.01); *A61L 27/38* (2013.01); *A61L 31/022* (2013.01); *A61L 31/088* (2013.01); *B22F 1/0025* (2013.01); *B22F 1/025* (2013.01); *B82Y 30/00* (2013.01); *C12M 25/00* (2013.01); *A61F 2002/3084* (2013.01); *A61L 2400/12* (2013.01); *A61L 2430/02* (2013.01); *A61L 2430/24* (2013.01); *A61L 2430/38* (2013.01); *Y10T 428/12028* (2015.01); *Y10T 428/24893* (2015.01); *Y10T 428/24909* (2015.01); *Y10T 428/25* (2015.01); *Y10T 428/26* (2015.01); *Y10T 428/31678* (2015.04)

(58) Field of Classification Search
None
See application file for complete search history.

(56) References Cited

U.S. PATENT DOCUMENTS

| 8,470,600 | B2 | 6/2013 | Duch et al. |
| 9,775,932 | B2 | 10/2017 | Desai et al. |
| 2005/0165472 | A1 | 7/2005 | Glocker |
| 2009/0220561 | A1* | 9/2009 | Jin et al. ............... 424/423 |
| 2011/0137419 | A1 | 6/2011 | Wong |
| 2011/0159070 | A1 | 6/2011 | Jin et al. |

(Continued)

FOREIGN PATENT DOCUMENTS

| JP | 2005246036 | 9/2005 |
| JP | 2007255832 | 10/2007 |
| JP | 2008294495 | 12/2008 |

(Continued)

OTHER PUBLICATIONS

Sul, Young-Taeg. "Electrochemical growth behavior, surface properties, and enhanced in vivo bone response of TiO2 nanotubes on microstructured surfaces of blasted, screw-shaped titanium implants." International journal of nanomedicine 5 (2010): 87.*
Textor, Marcus, et al. "Properties and biological significance of natural oxide films on titanium and its alloys." Titanium in medicine. Springer Berlin Heidelberg, 2001. 171-230.*
Kihwan Moon, International Preliminary Report on Patentability, PCT/US2013/025090, The International Bureau of WIPO, Date of Issuance: dated Aug. 12, 2014.
Kim, Seung Beom, International Search Report, PCT/US2013/025090, dated May 15, 2013, Korean Intellectual Property Office.

(Continued)

*Primary Examiner* — John Pak
*Assistant Examiner* — Daniel L Branson
(74) *Attorney, Agent, or Firm* — Greer, Burns & Crain, Ltd.; Gregory P. Einhorn

(57) ABSTRACT

In alternative embodiments, the invention provides products (articles) of manufacture comprising nanostructures such as nanotubes having a surface comprising tantalum. In alternative embodiments, products of manufacture of the invention include nanostructures, e.g., nanotubes, nanowire, nanopore, and the like comprising a surface layer of tantalum. In alternative embodiments, products or articles of manufacture of the invention are bioimplants, and the tantalum-surface-coated nanostructures of the invention provide increased bioactivity and bone forming ability. In alternative embodiments, products or articles of manufacture of the invention, e.g., bioimplants, comprising the tantalum-surface-coated nanostructures of the invention are used for in vitro, ex vivo and in vivo testing, implants, biomedical devices and therapeutics.

29 Claims, 18 Drawing Sheets

(56) References Cited

U.S. PATENT DOCUMENTS

2011/0160869 A1 6/2011 Duch et al.
2012/0239162 A1 9/2012 Liu et al.

FOREIGN PATENT DOCUMENTS

WO 2008115883 A1 9/2008
WO 2013119772 A1 8/2013

OTHER PUBLICATIONS

Kim, Seung Beom, International Search Report and Written Opinion, PCT Application No. PCT/US2013/025090, Korean Intellectual Property Office, dated May 14, 2013
Stella, et al., Preparation and properties of thin amorphous tantalum films formed by small e-beam evaporators, J. Phys. D: Appl Phys 42 (2009) 135417 (9pp).
Extended European Search Report for EP13746674.4, dated Aug. 25, 2015, 7 pages.
Dolatshahi-Pirouz et al., Fibronectin Adsorption, Cell Adhesion, and Proliferation on Nanostructured Tantalum Surfaces, ACS Nano, vol. 4, No. 5, May 25, 2010, pp. 2874-2882.
Maho et al., Tantalum oxide/carbon nanotubes composite coatings on titanium, and their functionalization with organophosphonic molecular films: A high quality scaffold for Hydroxyapatite growth, J. of Colloid and Interface Science 371, 2012, pp. 150-158.
Materials and Coatings for Medical Devices: Cardiovascular ASM Materials for Medical Devices Database Committee, ASM International, Ohio, USA, (2009), pp. 124-129.
Australian Examination Report No. 1, AU 2013217081, dated Nov. 12, 2015, 3 pages.
Yamamoto, Notice for Reasons for Rejection for JP 2014-555867, dated Sep. 11, 2017.

* cited by examiner

IMPLANTS HAVING TANTALUM COATED NANOSTRUCTURES

RELATED APPLICATIONS

This United States utility patent application incorporates by reference and is the § 371 national phase of PCT international patent application no. PCT/US2013/025090, having an international filing date of Feb. 7, 2013, which claims the benefit of priority under 35 U.S.C. § 119(e) of U.S. Provisional Application No. 61/596,143, filed Feb. 7, 2012. The aforementioned applications are expressly incorporated herein by reference in their entirety and for all purposes.

TECHNICAL FIELD

This invention generally relates to cell biology, medicine and nanotechnology. In alternative embodiments, the invention provides products (articles) of manufacture comprising nanostructures such as nanotubes having a surface comprising tantalum. In alternative embodiments, products of manufacture of the invention include nanostructures, e.g., nanotubes, nanowire, nanopore, and the like comprising a surface layer of tantalum. In alternative embodiments, products or articles of manufacture of the invention are bioimplants, and the tantalum-surface-coated nanostructures of the invention provide increased bioactivity and bone forming ability. In alternative embodiments, products or articles of manufacture of the invention, e.g., bioimplants, comprising the tantalum-surface-coated nanostructures of the invention are used for in vitro, ex vivo and in vivo testing, implants, biomedical devices and therapeutics.

BACKGROUND

Metallic tantalum (Ta) has been a biomaterial of recent interest for orthopedic applications, as it has been found to be highly corrosion resistant and bioinert, as well as bioactive in vivo, forming a bone-like apatite layer in simulated body fluid that biologically bonds to bone. Tantalum has regained interest in the biomaterials field mainly due to a new porous (trabecular) tantalum material of micro-porosity approved by the FDA in 1997, which has been shown to possess excellent osseointegrative properties. Since then, many studies have compared the biocompatibility, bacterial adherence and osteoconductivity of Ta with that of other common implant materials, such as Ti and CoCr. A recent demonstrated that porous Ta stimulates the proliferation and osteogenesis of osteoblasts from elderly female patients with compromised bone-forming abilities. However, despite the promising results to-date, the relatively expensive manufacturing cost, as well as the inability to produce a modular all-Ta implant has prevented its widespread acceptance. Tantalum is also a heavy metal with a density of 16.69 g/cm$^3$, almost four times heavier than Ti implants having a density of 4.51 g/cm$^3$. Such a heavy implant for orthopaedics application is not desirable. Tantalum metal is also much more expensive than titanium metal.

SUMMARY

In alternative embodiments, the invention provides products of manufacture, products, compositions, articles of manufacture, devices or implants, comprising:
a nanostructure or a nanoarchitecture,
wherein the nanostructure or nanoarchitecture is covered or coated: in part, on substantially all, or on all of its surface: a coating or outer covering or outer layer comprising in whole or in its substantial entirety, or in part, a tantalum (Ta), a Ta or Ta alloy, a Ta oxide or Ta$_2$O$_5$ coating, a crystalline tantalum (Ta), or an amorphous Ta,
wherein optionally the coating, outer covering or outer layer comprises or is composed of at least about 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or more of a tantalum (Ta), a Ta alloy, a Ta or Ta alloy oxide or Ta$_2$O$_5$ coating, a crystalline tantalum (Ta), or an amorphous Ta,
and optionally at least about 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or more, or up to about 99.9% or more, or between about 1% and 99.5%, of the nanostructure or nanoarchitecture is covered, coated or layered with a tantalum (Ta), a Ta alloy, a Ta or Ta alloy oxide or Ta$_2$O$_5$ coating, a crystalline tantalum (Ta), or an amorphous Ta,
and optionally at least about 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or more, or up to about 99.9% or more, or between about 1% and 99.5%, of: the product, article of manufacture, device or implant; or a surface of the product, article of manufacture, device or implant; or coating or outer covering, outer layer or outer surface of the product, article of manufacture, device or implant, is covered, coated or layered with the nanostructure or a nanoarchitecture.

In alternative embodiments, the products of manufacture, products, compositions, articles of manufacture, devices or implants of the invention further comprise or have on a surface a microscale structure or a plurality of microscale structures, and optionally at least about 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or more, or up to about 99.9% or more, or between about 1% and 99.5%, of the microscale structure or structures is covered, coated or layered with the nanostructure or a nanoarchitecture.

In alternative embodiments, the products of manufacture, products, compositions, articles of manufacture, devices or implants of the invention are manufactured as or for use as: a biomedical device or implant; an orthopaedic, dental, spinal, knee, joint or equivalent implant; or bone pin, an intramedullary rod, an intramedullary nail (IM nail) or inter-locking nail or Küntscher nail; or a bone or a tooth implant; or a joint replacement implant; or a pin, a plate or a post, or an equivalent.

In alternative embodiments, the nanostructure or a nanoarchitecture comprises: a nanotube, a nanopillar, a nanoribbon, a nanowire, a nanorod or a nanofiber or equivalents thereof; or, a plurality of nanotubes, nanoribbons, nanopillars, nanorods, nanofibers, or nanowires or equivalents thereof; or, an array of nanopillar, nanoribbon, nanotube, nanofiber, nanorod or nanowire or combination thereof structures,
and optionally the array is a vertically aligned array or substantially vertically aligned array,
and optionally the array of nanopillar, nanoribbon, nanotube, nanofiber, nanorod or nanowire or combination thereof structures has an average diameter in a range of between about 20 to 800 nm, and has an average height in a range of between about 50 to 2,000 nm.

In alternative embodiments, the thickness of the coating or outer covering or outer layer of tantalum (Ta), Ta alloy, Ta or Ta alloy oxide, or $Ta_2O_5$, crystalline Ta, or amorphous Ta, is:

at most about 0.1 mm (100 micrometer), 0.2, 0.3, 0.4, 0.5, 0.6, 0.7, 0.8, 0.9 or 1.0 mm; or less than about 0.01 mm (10 micrometer), 0.02, 0.03, 0.04, 0.05, 0.06, 0.07, 0.08, 0.09 or 0.10 mm; or less than about 1, 2, 3, 4, 5, 6, 7, 8, 9 or 10 micrometer; or less than about 0.1 micrometer (100 nm), 0.2, 0.3, 0.4, 0.5, 0.6, 0.7, 0.8, 0.9 or 1.0 nm; or the minimal thickness of is at least about 1, 2, 3, 4, 5, 6, 7, 8, 9 or 10 nanometers (nm).

In alternative embodiments, the products of manufacture, products, compositions, articles of manufacture, devices or implants of the invention further comprise:

(a) a cell or a plurality of cells, wherein optionally the cell or cells are: human cells; or stem cells; or chondrocytes, fibroblasts, osteoclasts or osteoblasts; or a cell involved in odontogenesis or bone formation; or bone cells, muscle cells, liver cells, liver parenchymal cells, endothelial cells, adipocytes, fibroblastic cells, Kupffer cells, kidney cells, blood vessel cells, skin cells, periodontal cells, odontoblasts, dentinoblasts, cementoblasts, enameloblasts or odontogenic ectomesenchymal tissue; or, any combination thereof, wherein optionally the cell or cells are adhered to or growing on the surface of the nanostructure or nanoarchitecture; and/or (b) a bone or a cartilage, or a grown and adhered bone structure, wherein optionally the bone or adhered bone structure comprises in whole or in part an orthopaedic bone, a dental bone, a spinal bone, a human or an animal bone, and optionally the bone or cartilage, or grown and adhered bone structure is on the top or outer surface of a Ta or a Ta oxide coating.

In alternative embodiments, the coating, outer covering, outer surface or outer layer is added by a physical vapor deposition process, a sputtering or evaporation process, or laser ablation or plasma spray process, or a chemical vapor deposition process, or by a chemical/electrochemical deposition process.

In alternative embodiments, the product, article of manufacture, device or implant comprises; or, a base or outer surface or outer layer of the product, article of manufacture, device or implant comprises; or, the nanostructure or a nanoarchitecture or nanostructure or a nanoarchitecture base comprises:

a metal, a titanium (Ti), a titanium oxide, a $TiO_2$, or a combination thereof;

an alloy containing or comprising a Ti or a Ti oxide by at least about 40%, 45%, 50%, 55%, 60%, 65%, 70%, 75% or more by weight, and optionally comprising alloying elements;

a metallic component, a $ZrO_2$, a $HfO_2$, a NbO or a $Nb_2O_5$, a $MoO_2$ or a $MoO_3$, a $VO_2$ or a $V_2O_5$, a $WO_2$ or a $WO_3$, or any alloy or oxide thereof, or an oxide thereof, or a Ti, Zr, Hf, Nb, Mo, V or W oxide, optionally by at least about 40%, 45%, 50%, 55%, 60%, 65%, 70%, 75% or more by weight, wherein optionally the metallic component comprises a plurality of metals or elements or comprises: Al, Ag, C, F, Mg, Ca, Si, P, Mn, Fe, Co, Cu, Zn, Pd, Ag, In, Sn, Sb, Re, Os, Ir, Pt, Au or Bi or one or more of rare earth elements or a combination thereof; or a stainless steel, a Si, a Si oxide, a carbon, a diamond, a noble metal, an Au, a Ag, a Pt, or their alloys, or a composite metal, a zirconia or zirconia or any alloy or oxide thereof, a cobalt-chrome alloy, a ceramic or a polymer or a plastic material, or any combination thereof.

In alternative embodiments, the nanostructure, nanoarchitecture or nanotube is anodized;

and optionally the nanostructure, nanoarchitecture or nanotube is a nanostructure, nanoarchitecture or nanotube layer or array formed by anodizing of the surface of a Ti metal or a Ti containing alloy, or a nanostructure, nanoarchitecture or nanotube layer or array formed by anodizing of a coated thick film layer of a Ti or a Ti-containing alloy on a non-Ti containing substrate, base, surface or implant.

In alternative embodiments, the products of manufacture, products, compositions, articles of manufacture, devices or implants of the invention further comprise: a chemical, a compound, a small molecule, an agent, an active agent, a biological agent, a drug, a tracer, wherein optionally the chemical, compound, small molecule, agent, active agent, biological agent, drug or tracer comprises: a peptide, a protein, a polypeptide, an antibody, a nucleic acid, a DNA or an RNA, an miRNA, an siRNA, a gene, a vector, a polysaccharide, a lipid, a growth factor, a cytokine, an antibiotic, a hormone, a therapeutic drug, a functional particle, a magnetic particle, a metallic particle, ceramic particle, a polymer particle or a combination thereof;

and optionally the chemical, compound, small molecule, agent, active agent, biological agent, drug or tracer is stored in or within a nanotube or a hollow nanowire or nanopillar, or between the spaces of or within or adhered on the nanostructure or a nano architecture;

and optionally the nanostructures or nanoarchitectures form a plurality of nanodepots by storing the chemical, compound, small molecule, agent, active agent, biological agent, drug or tracer: within (as in a nanowire, or in a hollow nanotube or nanopillar); or, between the nanostructures or nanoarchitectures; or, on the nanostructures or nano architectures;

and optionally the nanostructures or nanoarchitectures further comprise partially blocked or constricted, or triggerable or actuable, or partial bottlenecking configuration, openings, to allow the release of the chemical, compound, small molecule, agent, active agent, biological agent, drug or tracer, in a triggerable, actuable, controlled or slow release fashion, and optionally an entrance dimension of a nanodepot is reduced by selective deposition of metal or oxide material to induce partial bottlenecking configuration to slow down the release rate of the chemical, compound, small molecule, agent, active agent, biological agent, drug or tracer stored within, and optionally functional particles can be made of magnetic oxide particles or metallic particles are utilized for remotely actuated RF heating and creation of temperature gradient for accelerated or switch-on, switch-off release of the biological agents stored in the nanodepot space.

In alternative embodiments, the invention provides an in vitro, ex vivo or in vivo cell culture substrate or substrates for: new or enhanced cell growth; new or enhanced osteoblast, odontoblast, dentinoblasts or cementoblast growth; new or enhanced bone or cartilage growth; and/or, new or enhanced formation of a mineralized matrix, wherein the culture substrate or substrate surface comprises:

(a) a nanostructure or a nanoarchitecture,
wherein the nanostructure or nanoarchitecture is covered or coated: in part, on substantially all, or on all of its surface: a coating or outer covering or outer layer comprising in whole or in its substantial entirety, or in part, a tantalum (Ta), a Ta alloy, a Ta oxide or $Ta_2O_5$ coating, a tantalum (Ta), or a Ta alloy or a Ta alloy oxide,
wherein optionally the coating, outer covering or outer layer comprises or is composed of at least about 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or more of a tantalum (Ta), a Ta alloy, a Ta oxide or $Ta_2O_5$ coating, a crystalline tantalum (Ta), an amorphous Ta, or a Ta alloy or a Ta alloy oxide,
and optionally at least about 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or more, or up to about 99.9% or more, or between about 1% and 99.5%, of the nanostructure or nanoarchitecture is covered, coated or layered with a tantalum (Ta), a Ta alloy, a Ta oxide or $Ta_2O_5$ coating, a crystalline tantalum (Ta), an amorphous Ta, or a Ta alloy or a Ta alloy oxide; or (b) a nanostructure- or a nanoarchitecture-comprising surface as set forth in any of claims 1 to 10.

In alternative embodiments, the invention provides: an in vitro, ex vivo or in vivo supportive scaffolding for: new or enhanced cell growth; new or enhanced osteoblast, odontoblast, dentinoblasts or cementoblast growth; new or enhanced bone or cartilage growth; and/or, new or enhanced formation of a mineralized matrix, comprising:

a scaffolding surface comprising;
(a) a nanostructure or a nanoarchitecture,
wherein the nanostructure or nanoarchitecture is covered or coated: in part, on substantially all, or on all of its surface: a coating or outer covering or outer layer comprising in whole or in its substantial entirety, or in part, a tantalum (Ta), a Ta alloy, a Ta oxide or $Ta_2O_5$ coating, a tantalum (Ta), or a Ta alloy or a Ta alloy oxide,
wherein optionally the coating, outer covering or outer layer comprises or is composed of at least about 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or more of a tantalum (Ta), a Ta alloy, a Ta oxide or $Ta_2O_5$ coating, a crystalline tantalum (Ta), an amorphous Ta, or a Ta alloy or a Ta alloy oxide,
and optionally at least about 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or more, or up to about 99.9% or more, or between about 1% and 99.5%, of the nanostructure or nanoarchitecture is covered, coated or layered with a tantalum (Ta), a Ta alloy, a Ta oxide or $Ta_2O_5$ coating, a crystalline tantalum (Ta), an amorphous Ta, or a Ta alloy or a Ta alloy oxide; or (b) a nanostructure- or a nanoarchitecture-comprising surface as set forth in any of claims 1 to 11.

In alternative embodiments, of a product, article of manufacture, device or implant of the invention, or an in vitro, ex vivo or in vivo culture substrate or substrate of the invention, or an in vitro, ex vivo or in vivo supportive scaffolding of the invention:

the product, article of manufacture, device or implant; or, culture substrate or substrate; or, the supportive scaffolding: is on or part of an implant for a bone implant or bone onlay or bone support site, wherein optionally the bone implant, onlay or support is fabricated for, or is to replace all or part of, a:

a finger joint repair or replacement,
a wrist repair or replacement,
an elbow repair or replacement,
a shoulder repair or replacement,
a leg repair or replacement,
an arms repair or replacement,
a hip repair or replacement,
a knee repair or replacement,
an ankle repair or replacement,
a foot or a toe repair or replacement,
an intervertebral disc of a spinal cord repair or replacement,
a rib cage repair or a rib replacement,
a skull mesh, patch or replacement,
a pin, a mesh or a rod, or
a rod, a screw or a bone stabilizer implant.

In alternative embodiments, the invention provides methods for starting or inducing new or enhanced cell growth; new or enhanced osteoblast, odontoblast, dentinoblasts or cementoblast growth; new or enhanced bone or cartilage growth; and/or, new or enhanced formation of a mineralized matrix, comprising implanting in vivo a (a) a nanostructure or a nanoarchitecture,
wherein the nanostructure or nanoarchitecture is covered or coated: in part, on substantially all, or on all of its surface: a coating or outer covering or outer layer comprising in whole or in its substantial entirety, or in part, a tantalum (Ta), a Ta alloy, a Ta oxide or $Ta_2O_5$ coating, a tantalum (Ta), or a Ta alloy or a Ta alloy oxide,
wherein optionally the coating, outer covering or outer layer comprises or is composed of at least about 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or more of a tantalum (Ta), a Ta alloy, a Ta oxide or $Ta_2O_5$ coating, a crystalline tantalum (Ta), an amorphous Ta, or a Ta alloy or a Ta alloy oxide,
and optionally at least about 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or more, or up to about 99.9% or more, or between about 1% and 99.5%, of the nanostructure or nanoarchitecture is covered, coated or layered with a tantalum (Ta), a Ta alloy, a Ta oxide or $Ta_2O_5$ coating, a crystalline tantalum (Ta), an amorphous Ta, or a Ta alloy or a Ta alloy oxide;

(b) a nanostructure- or a nanoarchitecture-comprising surface as set forth in any of claims 1 to 10; or (c) a product, article of manufacture, device or implant of any of claims 1 to 10, or the in vitro, ex vivo or in vivo culture substrate or substrate of claim 11, or the in vitro, ex vivo or in vivo supportive scaffolding of claim 12.

In alternative embodiments, the invention provides methods of fabricating a bone-enhancing nanotube or nanopillar configuration using anodization, formation and selective phase removal of a two-phase mask layer, comprising: using diblock copolymer layer, spinodally decomposing alloy layer, or two-phased alloy film, followed by selective etching of the biomaterial surface to produce nanotube or nanopillar surface configurations.

The details of one or more embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

BRIEF DESCRIPTION OF THE DRAWINGS

The drawings set forth herein are illustrative of embodiments of the invention and are not meant to limit the scope of the invention as encompassed by the claims.

Like reference symbols in the various drawings indicate like elements.

FIG. 1(a)-(b): Schematically illustrates exemplary devices of the invention comprising self-organized $TiO_2$ nanotube arrays formed on titanium substrate with a thin film of Ta deposited on the nanotube surfaces to accelerate osteoblast proliferation and bone osseointegration: FIG. 1(a) illustrates laterally-spaced vertically oriented $TiO_2$ nanotube arrays, and the exemplary process for deposition of a thin film coating of Ta on the nanotubes comprising a sputtering or an evaporation process, and the final product comprising nanotubes (in this example, configured as a nanotube array), coated with, or having a thin film coating of Ta, the figure noting that a device of the invention can comprise any nanostructure having a Ta coating, e.g., as a thin film coating.

FIG. 4(a) schematically illustrates exemplary devices of the invention comprising Ta coated nanopillars, which can be Ta coated $TiO_2$ nanopillar arrays, on a substrate, which can be a titanium substrate; FIG. 4(b) schematically illustrates one embodiment where Ta coated $TiO_2$ nanopillar arrays further comprise osteoblast cells, and the exemplary device of the invention can accelerate osteoblast proliferation and bone osseointegration. Spacing between the Ta coated nanopillars can provide for flow of nutrients, etc. to the cells growing on the Ta coated nanopillars; and in one embodiment, where extracellular matrix can also grow on (or be applied to) the Ta coated nanopillars.

FIG. 5(a) schematically illustrates nanostamping of a Ti or an alloyed Ti base to make exemplary devices of the invention, where the optional use of a making polymer is also illustrated; FIG. 5(b) schematically illustrates both: chemical or reactive ion etching (RIE) of Ti nanopillars, followed by Ta or $Ta_2O_6$ sputter coating of the nanopillar arrays.

FIG. 6(a) schematically illustrates the starting material or substrate, e.g., comprising titanium (Ti) for use as, e.g., in alternative embodiments, an implant for bone growth; FIG. 6(b) schematically illustrates coating of textured material, for example, coating by co-sputter layering, decomposable diblock copolymer, spinodally decomposing alloy, and the like; FIG. 6(c) schematically illustrates an exemplary "nanoisland" mask coating procedure left after preferential etching away of one of the two phases; FIG. 6(d) schematically illustrates an exemplary mask coating procedure comprising etching of a Ti or Ti alloy through the masking islands for formation of exemplary nanopillar arrays of the invention; FIG. 6(e) schematically illustrates removal of the coating; and, FIG. 6(f) schematically illustrates the optional step of additional etching or anodization to produce deeper nanopillar or nanotubes on the surface of the device of the invention, which in alternative embodiments can be an implant.

FIG. 9(a) illustrates SEM micrographs at 2000× of HOb cells cultured on the nanotube surfaces (Ti, $TiO_2$ nanotubes (NT), Ta, and Ta-coated nanotubes (NT)), the image showing larger bone nodule formation on the Ta-coated NT surface after 3 weeks, Scale bar=10 µm; FIG. 9(b) graphically illustrates data from an energy dispersive x-ray (EDX) analysis of the atomic percent of calcium and phosphorous mineral elements on the surfaces (n=5), the bar graph shows the mean±standard error bars; the p-values after performing an ANOVA test reached statistical significance (p≤0.001), as indicated by (*); amounts of P and Ca were significantly higher on the Ta-coated surface.

FIG. 10(c) illustrates a table presenting corresponding rates (slopes of the linear trendlines) of phosphorus and calcium deposition for each substrate; the line graphs show the mean±standard error bars; the p-values after performing an ANOVA test reached statistical significance (p≤0.001) for all comparisons between samples except for Ti vs. Ta.

FIG. 12(a) schematically illustrates TiO$_2$ nanotubes with Ta or Ta$_2$O$_5$ surface coating on a Ti substrate; FIG. 12(b) schematically illustrates the embodiment wherein one or more agents, e.g., biological agents, e.g., polypeptides, growth factors, hormones or steroids, nucleic acids or DNA, collagen, antibiotics, nanoparticles, and the like, are stored in the vertically aligned nanotube pores, e.g., stored in the so-called "nano-depots"; FIG. 12(c) schematically illustrates the alternative embodiment comprising use of diameter-reducing structures on the outlet of the vertically aligned nanotube pores, e.g., as diameter-reducing structures on the nano-depot entrances for slower or controlled release of stored the stored agents, e.g., biological agents.

FIG. 12(a) schematically illustrates TiO$_2$ nanopillars with Ta or Ta$_2$O$_5$ surface coating; FIG. 12(b) schematically illustrates the embodiment wherein one or more agents, e.g., biological agents, e.g., polypeptides, growth factors, hormones or steroids, nucleic acids or DNA, collagen, antibiotics, nanoparticles, and the like, are stored in the gap between the nanopillars; FIG. 12(c) schematically illustrates the alternative embodiment comprising use of diameter-reducing structures, e.g., to create a dimension-reduced entrance for slower release of stored biological agents from the nanopillar gap.

FIG. 14(a) TiO$_2$ NTs, FIG. 14(b) as-deposited Ta-coated NTs, FIG. 14(c) metallic Ta-coated NTs, FIG. 14(d) oxidized Ta-coated NTs, FIG. 14(e) Ta$_2$O$_5$-coated NTs.

Figure 1:
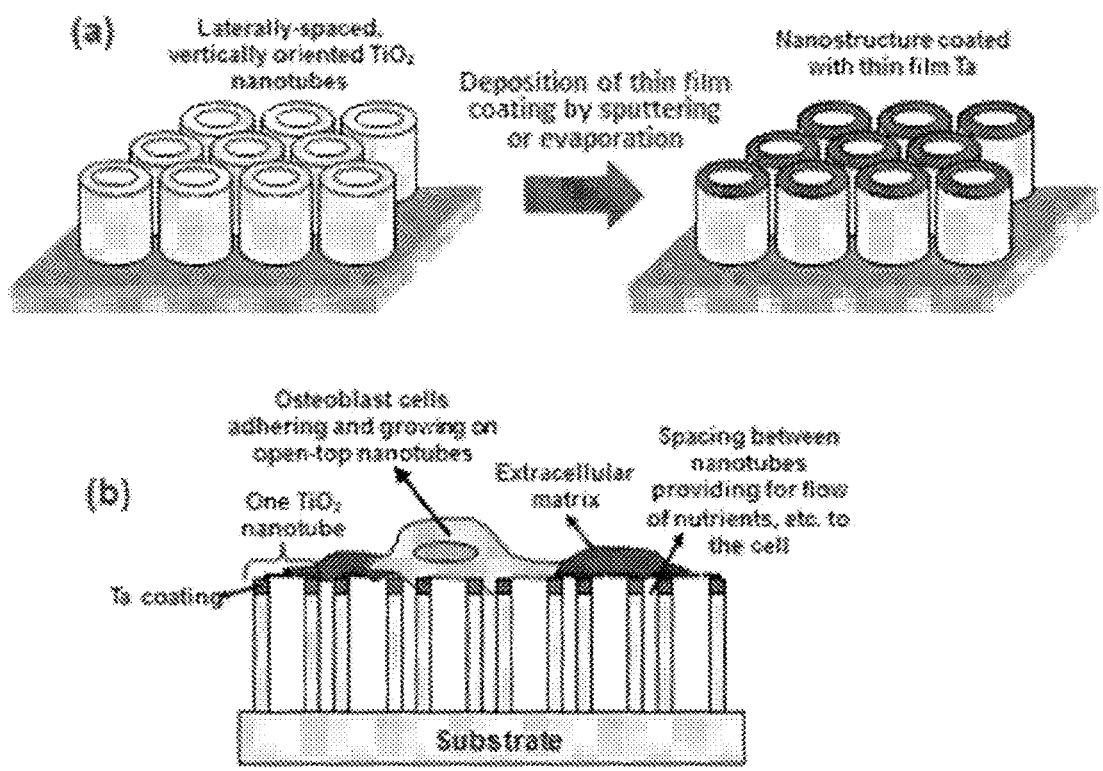
FIG. 1 (b), illustrates an exemplary use of a device of the invention, and an exemplary method of the invention, wherein in vivo, in vitro or in situ osteoblast cells adhere to and grow on the Ta coated nanostructures, in this example nanotubes configured as a nanotube array, and in one embodiment, where extracellular matrix can also grow on (or be applied to) the Ta coated nanostructures, and the spacing between the Ta coated nanostructures can provide for flow of nutrients, etc. to the cells growing on the Ta coated nanostructures.

It is to be understood that these drawings are for the purposes of illustrating the concepts of the invention and are not to scale. For example, the dimensions of some of the elements are exaggerated relative to other elements.

Reference will now be made in detail to various exemplary embodiments of the invention, examples of which are illustrated in the accompanying drawings. The following detailed description is provided to give the reader a better understanding of certain details of aspects and embodiments of the invention, and should not be interpreted as a limitation on the scope of the invention.

DETAILED DESCRIPTION

In alternative embodiments, the invention provides products or articles of manufacture, including implants, particles, spheres and the like, comprising a thin, conformal layer of tantalum. In alternative embodiments, the invention provides nanostructures, e.g., nanotubes, nanowire, nanopore, and the like comprising a surface conformal layer of tantalum on the nanotopography. In alternative embodiments, the invention provides nanostructures, e.g., nanotubes, nanowire or nanopore arrays with a thin, conformal layer of tantalum on the nanotopography. In alternative embodiments, products or articles of manufacture of the invention, e.g., bioimplants, and the tantalum-surface-coated nanostructures of the invention provide increased bioactivity and bone forming ability. In alternative embodiments, products or articles of manufacture of the invention, e.g., bioimplants, and the tantalum-surface-coated nanostructures of the invention are used for in vitro, ex vivo and in vivo testing, implants, biomedical devices and therapeutics.

In alternative embodiments, products or articles of manufacture provide improved bone formation using the tantalum-coated (Ta-coated) $TiO_2$ nanotubes on Ti implants. It was demonstrated that Ti implants of the invention comprising tantalum-coated (Ta-coated) $TiO_2$ nanotubes provide improved bone formation for both animal (mouse) bone cells and human bone cells (human osteoblast) as compared to use of $TiO_2$ nanotubes alone. It was determined that both surfaces instigate equivalent levels of cell adhesion, proliferation, and morphology. At advanced culture times, the osteo-functionality was enhanced on the Ta surface in terms of alkaline phosphatase activity, bone nodule formation, and matrix mineral deposition. In alternative embodiments, the tantalum-coated (Ta-coated) $TiO_2$ nanotubes of the invention are applied advantageously to orthopedic and dental implants. In alternative embodiments, products or articles of manufacture of the invention are biomedical implants, e.g., bone or tooth implants, or joint replacement implants, or pins, plates or posts and the like where bone deposition is desired.

In alternative embodiments, the invention provides nanostructured products of manufacture and biomaterials comprising a partially, substantially or completely tantalum-coated (Ta-coated) surface, devices comprising such biomaterials. In alternative embodiments, using products of manufacture and biomaterials of the invention, the invention also provides fabrication methods for efficient production of bone in the human and animal body. In alternative embodiments, nanostructured products of manufacture and biomaterials enable accelerated osteoblast cell growth and bone mineralization, and also are fabricated to allow release of growth factors and other chemical or biological materials stored in the nano-depot of the nanostructured biomaterial surfaces.

In alternative embodiments, the invention provides titanium oxide nanostructures, e.g., nanotubes, nanowires, and the like, comprising a partially, substantially or completely tantalum-coated (Ta-coated) surface. These compositions of the invention comprise nanosubstrates that enhances bone growth.

In alternative embodiments, the invention provides methods and structures that combine Ti and/or $TiO_2$, which are much lighter material than tantalum, and a tantalum-coated (Ta-coated) surface. In alternative embodiments, the $TiO_2$ nanotube geometry enhances bone growth and stem cell differentiation, and the invention combines the advantages of the $TiO_2$ nanotubes together with the chemical properties of a Ta surface.

In alternative embodiments, the use of a restricted amount of tantalum is essential to minimize the implant becoming heavy and costly. Therefore, in alternative embodiments Ta is added as a thin coating material on a base structure comprising nanotubes or nanostructures of metals, ceramics and/or polymers, and the like. In alternative embodiments, the thickness of the Ta surface coating therefore is at most 0.1 mm (100 micrometer), or less than 0.01 mm (10 micrometer), or less than 1 micrometer, or less than 0.1 micrometer (100 nm). In alternative embodiments, the minimal thickness of Ta coating is at least 5 nanometers (nm).

In alternative embodiments the Ta coating is added by physical vapor deposition such as sputtering or evaporation, or by chemical vapor deposition, or by chemical/electrochemical deposition.

In alternative embodiments, bone-inducing substrate materials are incorporated in the surface configurations of nanotubes and nanopillars, with Ta or Ta oxide surface coatings. The nanostructured substrate in the case of the invention is Ti and Ti oxide as well as alloys containing Ti or Ti oxide by at least 50% weight.

In alternative embodiments, in addition to the Ta film deposition on the surface, e.g., on a Ti or $TiO_2$ nanotube or other nanostructure, other desirable orthopaedic, dental, spinal, knee or other implant substrate materials for Ta metal deposition are used, e.g., including nanotubes or other nanostructures such as those made from alloyed Ti, including Ti-6Al-4V alloy, and nanotubes or other nanostructures made from $ZrO_2$, $HfO_2$, NbO or $Nb_2O_5$, $MoO_2$ or $MoO_3$, $VO_2$ or $V_2O_5$, $WO_2$ or $WO_3$, or nanotubes or other nanostructures made of alloy oxides comprising the metallic component being at least 50% weight of one or more of Ti, Zr, Hf, Nb, Mo, V, W, oxides, with the remaining metallic component selected from one or more of various other metals or elements such as Al, Ag, C, F, Mg, Ca, Si, P, Mn, Fe, Co, Cu, Zn, Pd, Ag, In, Sn, Sb, Re, Os, Ir, Pt, Au, Bi, and one or more of rare earth elements. Other materials such as stainless steels, Si, Si oxide, carbon, diamond, noble metals (such as Au, Ag, Pt and their alloys), polymer or plastic materials, or composite metals, ceramics or polymers can also be utilized to produce and use similar desired surface configurations for bioimplant and cell growth applications; and in alternative embodiments, a coating of nanostructured Ta or Ta oxide with a thickness of at least about 5 nm and the coating coverage of at least 80% of the total surfaces is used.

In alternative embodiments, the invention provides materials, fabrication methods, and therapeutic applications of bone-inducing biomaterials substrate based on nanostructured surfaces, in particular, with Ti oxide based nanotube or nanopillar configurations with a Ta or Ta oxide surface coating.

In alternative embodiments, the products of manufacture of the invention, e.g., devices, biomaterials or implants, are fabricated by anodization or nanomasked etching techniques.

In alternative embodiments, the products of manufacture of the invention, e.g., devices, biomaterials or implants, enable accelerated osteoblast cell growth and bone formation. In alternative embodiments, the products of manufacture of the invention, e.g., devices, biomaterials or implants, comprise nano-depots that allow the release of growth factors and other chemical or biological materials stored in the nano-depot of the nanostructured biomaterial surfaces. Other materials such as Ti alloy based oxides or containing Al, Zr, Hf, Nb, V, Mo, W based oxides, or stainless steel based alloys are also utilized as the underlying substrate material. In addition, the surface coating on the nanoarchitecture comprises oxidized Ta of various crystal structures, as well as amorphous Ta.

In alternative embodiments, the products of manufacture of the invention are bone-integrating biomaterials having Ta coated nanostructures that can be utilized for repair of bone at any orthopedic implant site, e.g., in the form of bone implant surface coatings to induce osseointegration to existing bone on the contact side.

In alternative embodiments, the products of manufacture of the invention comprise or are bone-inducing Ta-coated, nanoscale biomaterials that can be utilized as in vitro cell culture substrate for enhanced osteoblast growth and formation of mineralized matrix, followed by implantation into human or animal body. The inventive bone-inducing Ta-coated, nanoscale biomaterials can also be utilized for enhanced differentiation of mesenchymal or embryonic stem cells toward bone or cartilage cells.

In alternative embodiments, the products of manufacture of the invention comprise nano-depot configurations, e.g., on biomaterials comprising a Ta surface coating; and these nano-depot configurations can be utilized as a reservoir to store and slowly and continuously deliver growth factors, antibiotics, and other drugs and biochemicals for further therapeutic benefits for patients.

In alternative embodiments, the invention provides various methods of manufacture, methods of cell culturing, method of implant applications using products of manufacture of the invention, e.g., cell/bone-growth accelerating biomaterials or devices of the invention.

In alternative embodiments, the invention provides products (articles) of manufacture, e.g., biomaterials and implant, comprising Ta-coated titanium oxide nanotubes, ZrO2, HfO2, NbO or Nb2O5, MoO2 or MoO3, VO2 or V2O5, WO2 or WO3 nanotubes or nanowires, alternative metals and alloys. In alternative embodiments, the invention provides fabrication methods for these compositions, and applications and methods for these compositions of the invention, e.g., biomedical in vivo and in vitro applications for strongly adhered, and kinetically accelerated bone growth, cartilage growth, periodontal cell growth, organ cell growth (liver, kidney, etc.), drug toxicity testing, cell detection, artificial organs, etc. In alternative embodiments, the invention provides specific embodiments illustrated in the drawings of this invention.

In alternative embodiments, the invention provides bone growth enhancing biomaterials comprising nanotube or nanopillar architecture coated with a thin film of Ta or $Ta_2O_5$, the bulk of which is composed of Ti or $TiO_2$, or a similar structure made of oxides of alloys containing Ti or Ti oxide by at least 50% by weight, or a similar structure made of oxides of alloys containing Zr, Hf, Nb, Ta, Mo, V, W, by at least 50% weight, or a similar structure made of stainless steel, wherein the osteoblast functionality, as indicated by the degree of mineralized matrix formation, is increased by at least 10%, or by at least 30%, or by at least 50% as compared with the identical material without nanotube or nanopillar surface configurations.

In alternative embodiments, the invention provides bone growth enhancing biomaterials, wherein the dimension of the nanotube or nanopillar structure is controlled to certain ranges as indicated herein.

In alternative embodiments, the invention provides bone growth enhancing biomaterials, wherein the nanodepot space interior of the nanotubes or in the gap between the nanopillars is utilized as a reservoir, and stores and controllably deliver biological agents for further therapeutic benefits for patients. In alternative embodiments, the entrance dimension of the nanodepot is reduced by selective deposition of metal or oxide material to induce partial bottlenecking configuration to slow down the release rate of the biological agents stored. The agents can include growth factors, collagens, various proteins/biomolecules, genes, DNAs, antibiotics, hormones, therapeutic drugs, functional particles of magnetic, metallic, ceramic, polymer particles. The functional particles can be made of magnetic oxide particles or metallic particles are utilized for remotely actuated RF heating and creation of temperature gradient for accelerated or switch-on, switch-off release of the biological agents stored in the nanodepot space.

In alternative embodiments, the invention provides methods of fabricating bone-enhancing nanotube or nanopillar configuration using anodization, formation and selective phase removal of a two-phase mask layer using diblock copolymer layer, spinodally decomposing alloy layer, or two-phased alloy film, followed by selective etching of the biomaterial surface to produce nanotube or nanopillar surface configurations.

In alternative embodiments, the invention provides uses of bone-inducing implants, devices and biomaterials of the invention, wherein the use includes repair of bones or cartilages in finger, wrists, elbows, shoulders, legs, arms, hips, knees, ankles, feet or toes, intervertebral discs, or rib cage repair or replacement, as well as any rod, screw or other bone stabilizer implants. The compositions and methods of the invention enable joint or bone repair or replacement while providing the structural support and chemical environment for new bone matrix to grow, and hence can replace damaged, infected, aged, or diseased bone caused by various diseases such as osteoporosis, or an autoimmune disease in which the immune system attacks the body's cells and tissue, resulting in bone decay or damage.

In alternative embodiments, the invention provides in vivo uses of bone-integrating implants, devices and biomaterials of the invention, wherein the biomaterial is applied as a patch bone implant piece inducing strong osseointegration.

In alternative embodiments, the invention provides in vivo uses of bone matrix inducing implants, devices and biomaterials of the invention, wherein the biomaterial is utilized for osteoblast cell culture substrate for enhanced bone matrix production, preferably using the patient's own cells, followed by implanting into human or animal body near a region of bone damage.

In alternative embodiments, the invention provides non-metallic or non-Ti based substrates, the surfaces of which have been converted to $TiO_2$ type nanotubes or nanopores and coated with a thin Ta layer. In alternative embodiments, either a thin film coating of Ti or $TiO_2$ is applied onto the surfaces of already nanoporous material, or a thick film Ti is deposited and anodized to create $TiO_2$ nanotube type, so as to exhibit desirable cell or bone growth accelerating characteristics. In alternative embodiments, the invention provides porous or patterned substrates which have been made biocompatible and cell- or bone-growth-accelerating by $TiO_2$ surface nanotubes, etc., and various fabrication methods, and biomedical applications.

In alternative embodiments, the invention provides Ta coated biocompatible materials configured in loose particles, loose short-fibers, or loose flakes. In alternative embodiments, the powder surfaces are processed to comprise nano-pore or nanotube array nanostructure, so that the loose powders exhibit cell- or bone-growth-accelerating characteristics, which is useful for bone cement and other tissue connection applications. In alternative embodiments various types of fabrication methods for $TiO_2$ surface nanotubes on loose powders, short-fibers, flakes, fragmented mesh screens can be used. In alternative embodiments, various application methods, and biomedical applications including accelerated bone growth, dental bone growth, periodontal tissue growth are used.

In alternative embodiments, the invention provides Ta-coated biocompatible and cell-growth-enhancing culture substrate comprising elastically compliant protruding nanostructure substrate coated with Ti, $TiO_2$ or related metal and metal oxide films. In alternative embodiments, the invention provides elastically compliant protruding nanostructure substrate coated with Ti, $TiO_2$ or related metal and metal oxide films enhanced cell culture characteristics, various types of fabrication methods for such biocompatible and elastically compliant nanostructured cell-culture substrate, and their applications for in-vitro cell culture or in-vivo therapeutic applications.

In alternative embodiments, the invention provides methods of forming Ta-coating on implant surfaces using sputtering, evaporation, laser ablation, ion beam deposition, plasma spray, chemical vapor deposition, and the like.

In alternative embodiments, the invention provides articles, methods, and uses of preparing Ta-coated granules or particles of Ti, Zr, Hf, Nb, Mo, V or W, or their oxides for potential applications for dental bone repair, cure of osteoporosis, e.g., by electroplating, electrodeless plating, chemical vapor deposition, physical vapor deposition, sputtering, etc.

In alternative embodiments, the invention provides Ta-coated nanostructures, materials, various geometries, and various embodiments as set forth in the figures of the invention.

$TiO_2$ nanotubes can be prepared by various anodization processes. See articles by Gong, et al., *Journal of Materials Research*, Vol. 16, No 12, page 3331-3334 (2001), by J. M. Macak, et al., Angew. Chem. Int. Ed., vol. 44, page 7463-7465 (2005), Electrochimica Acta 50 (2005) 3679-3684 (2005), and Angew. Chem. Int. Ed., Vol. 44, 2100-2102 (2005), by A. Ghicov, et al., Electrochemistry Communications, Vol. 7, page 505-509 (2005) and by S. Oh et al, *Biomaterials*, Vol. 26, page 4938-4943 (2005).

In alternative embodiments, the structure of the anodized $TiO_2$ nanotube array, such as the diameter, spacing and height of nanotubes, is controllable during the electrochemical anodization process. In alternative embodiments the concentration of electrolytes is carefully chosen, as reported in articles by Gong, et al., Oh, et al, Macak, et al., and Ghicov, et al. mentioned above. Some exemplary electrolytes and their concentrations are: 0.5 wt % hydrofluoric acid (HF) in water, 0.5 wt. % ammonium fluoride ($NH_4F$) in 1 M ammonium sulphate (($NH_4)_2SO_4$), and 1 wt. % NaF in 1M $Na_2SO_4$ solution. Various anodization processing parameters such as the applied voltage, reaction time, the pH and the temperature of the bath, etc. have to controlled and optimized as well.

In alternative embodiments the base material for anodized nanotubes can be pure Ti or can be an alloy based on Ti such as Ti—V—Al alloys or other solid solution hardened or precipitation hardened alloys with increased mechanical strength and durability.

In alternative embodiments, while the specific examples of accelerated osteoblast cell bone-forming functionality and mineralized extracellular matrix formation are mostly on the substrate material of Ti and Ti oxide with a Ta thin film coating, other titanium alloys which may contain other elements but having Ti or Ti oxide by at least 50% weight also can be used as the underlying substrate. In alternative embodiments other transition or refractory metals such as Al, Zr, Hf, Nb, Ta, Mo, W, and their oxides, or alloys of these metals and oxides are used.

In alternative embodiments other materials such as stainless steels, Si, Si oxide, carbon, diamond, noble metals (such as Au, Ag, Pt and their alloys), polymer or plastic materials, or composite metals, ceramics or polymers, engineered into specific nanotube or nanopore array structure are utilized e.g. for bio implant and accelerated bone formation applications; and in alternative embodiments a preferential coating of Ta and Ta oxide with a thickness of at least 5 nm and the coating coverage of at least 80% of the total surfaces is used.

In alternative embodiments anodized aluminum oxide, which is formed by similar methods as anodized titanium oxide and results in a nanoporous array of highly defined features, is used as the underlying substrate for this invention. In alternative embodiments such a substrate is coated with Ta or Ta oxide in the same manner, and provide a highly bioactive, rapid bone-forming substrate.

Figure 3:
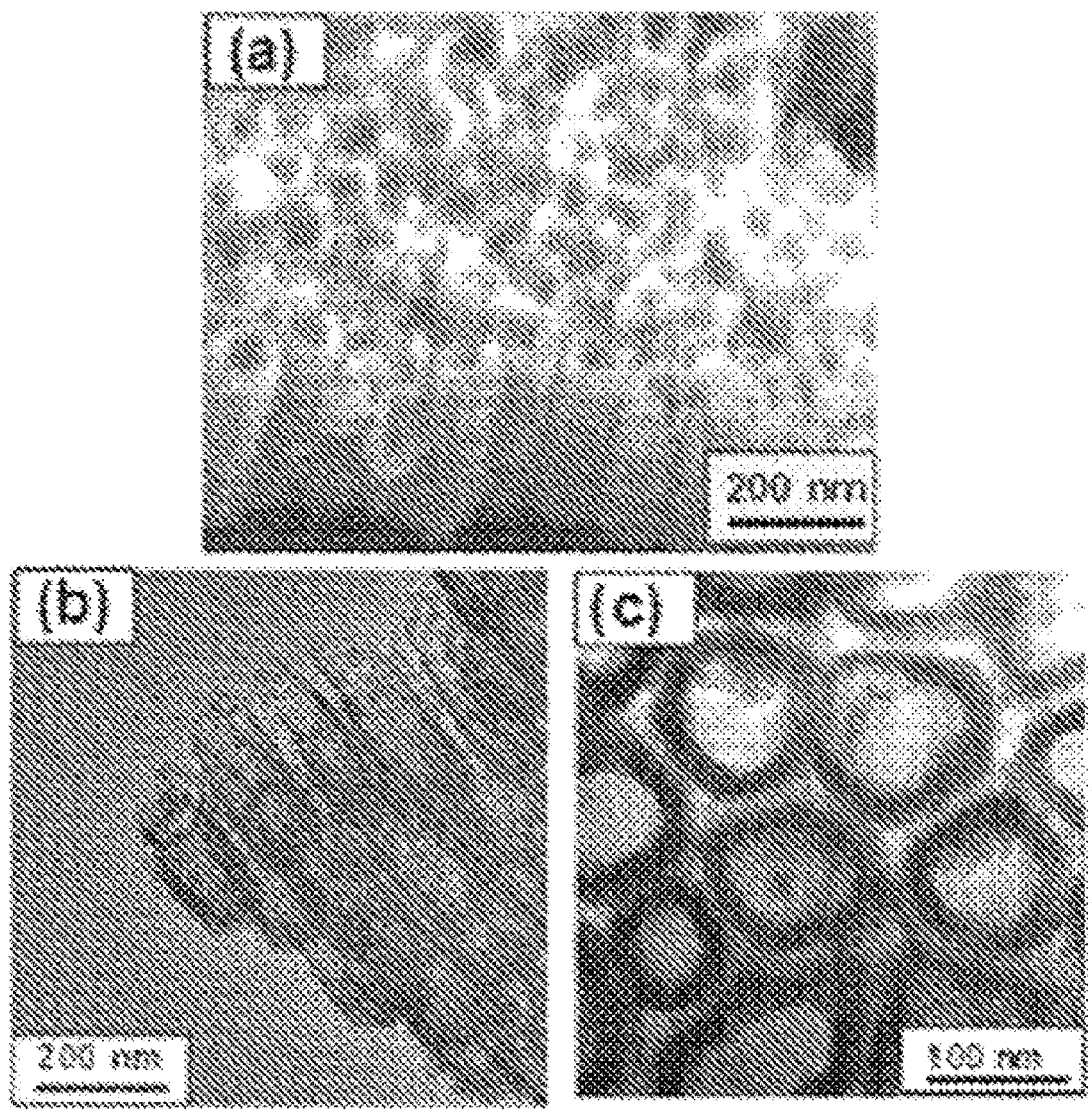
FIG. 3 illustrates: exemplary configurations of the anodization processed $TiO_2$ nanotube arrays showing (a) an oblique view scanning electron microscope (SEM) image (b) an transmission electron microscope (TEM) image in longitudinal direction, parallel to the nanotube alignment, (c) a cross-sectional view TEM image in perpendicular direction to the nanotube alignment.

An important factor for osteoblast cell growth and formation of mineralized matrix is a continuous supply of nutrients including proteins, mineral ions, fluid, etc. to the cell through the flow of body fluid. In alternative embodiments, the gap (spacing) between adjacent $TiO_2$ nanotubules, e.g., as in FIG. 1, serves such a function of allowing the body fluid to continuously pass through and supply nutrients to the bottom side of the growing cells. In alternative embodiments a desired gap between the nanotubules is in the range of about between about 2 to 100 nm, or between about 5 to 30 nm, as shown in FIG. 3 with exemplary micrographs of anodization processed $TiO_2$ nanotubes. Transmission electron microscope (TEM) photographs shown for an exemplary inventive $TiO_2$ nanotube array structure, FIGS. 3(b) and (c), show an average of approximately 15 nm spacing between the nanotubes.

Figure 4:
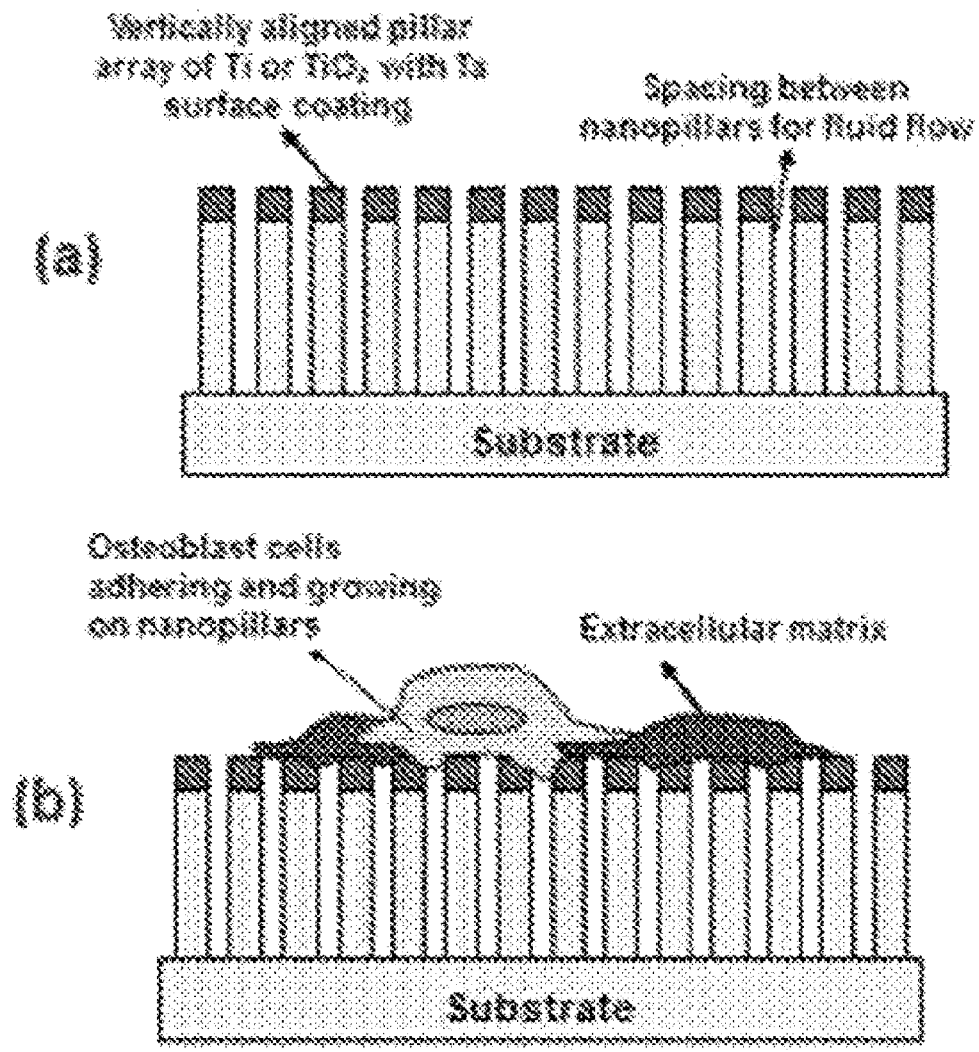
FIG. 4(a)-(b): schematically illustrates exemplary devices of the invention.

While the nanotube array configuration described above allows a continuous supply of cell grow nutrients, a nanopillar array configuration illustrated in FIG. 4 also performs similar function of continuous supply of cell grow nutrients, and its nanotopography structure and the gap between the nanopillars allows strong cell adhesion. Such a nanopillar structure can be formed on the surface of Ti, Zr, Hf, Nb, Ta, Mo, W, or their alloys, or a thin coating of these metals and alloys, by patterned masking and etching, or a combination of initial patterned etching and subsequent anodization. The nanostructured surface can then be coated with a thin film of Ta or Ta oxide, as in the case of the anodized nanotube array.

While Ti based implant or substrate is an exemplary substrate material onto which a nanostructure or nanoarchitecture of the invention formed, e.g., in one embodiment, prior to the coating of osteoblast or bone formation enhancing Ta or Ta oxide coating, other materials can also be utilized as the base implant or substrate. For example, in alternative embodiments, the nanotube formed by anodization, having vertically aligned configuration conformally formed on the local substrate surface, has a diameter in the range of between about 20 to 800 nm, and/or a height in the range of between about 50 to 2,000 nm; and can be formed on a bulk geometry substrate material, e.g., made of an oxide-containing Ti or other refractory metal containing at least about 50 wt % Ti, optionally containing one or more alloying elements.

In alternative embodiments, a nanostructure or a nanoarchitecture, e.g., a nanotube, can be formed by anodizing of the surface of a thick film Ti metal or Ti containing alloy, for example, having a thickness of between about 0.5 to 20 micrometer thick Ti metal layer deposited by e.g., a sputtering, evaporation, laser ablation, chemical vapor deposition, or plasma spray process, or combination thereof. Such a Ti metal layer can be coated on non-Ti containing substrates or implants, such as zirconia based implants (an example being zirconia ceramic based knee implants) or cobalt-chrome type or stainless steel type alloy based implants, or polymer based implants such as PolyEther EtherKetone (PEEK) type or ultra-high molecular weight polymer type implants, e.g., which can be useful for spine implants. In alternative embodiments, the coated Ti layer can then be anodized to form $TiO_2$ nanotubes onto which thin Ta or Ta oxide coating can be added for enhanced bone-forming characteristics.

Figure 5:
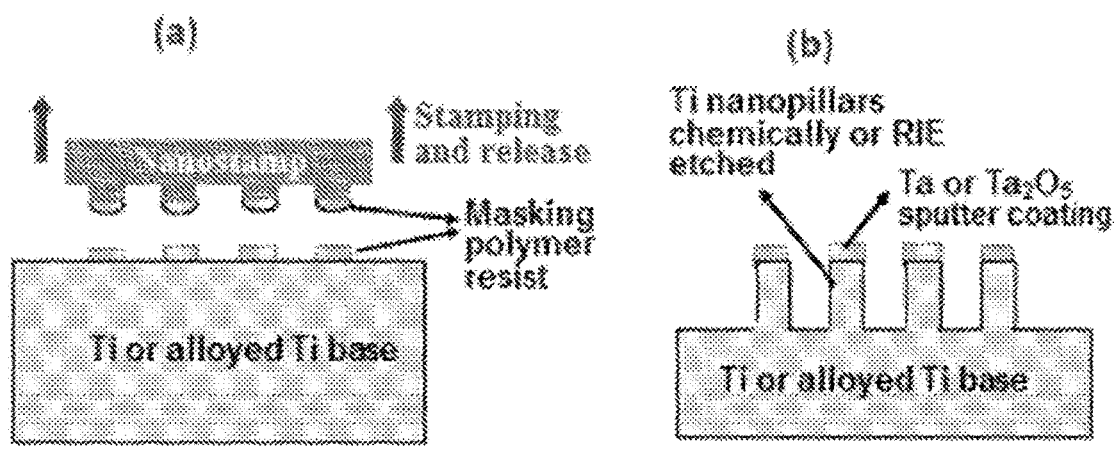
FIG. 5(a)-(b): schematically illustrate a "nanostamping" exemplary process for making devices of the invention.

One convenient way of fabricating the bone-enhancing nanopillar structure, in one embodiment, is to utilize nano-imprint technology. As illustrated in FIG. 5, nano stamping of polymer mask resist such as PMMA (polymethyl-methacrylate) layer can be carried out on the desired surface, in this case, Ti or related metal and alloy surface. The PMMA is first spin-coated into a thin layer, e.g., between about a 20 to 100 nm thick layer, then the nanostamp is pressed onto this uncured PMMA layer to pick up the resist islands, which is then imprinted on Ti or alloy surface to leave islands of PMMA mask. The Ti or alloy base is then chemically etched or reactive ion etched (RIE) to form the desired $TiO_2$ nanopillar structure. The pillars can be composed entirely of $TiO_2$ or only the surface of the pillars can be converted to $TiO_2$ by oxidation heat treatment of anodization treatment. The nanostamps can be made of patterned Si, metal or elastomer (PDMS), with the mechanically compliant elastomeric stamp allowing more reliable transfer of the masking resist islands. A thin film of Ta or Ta oxide can then be deposited on the nanopillar array.

Figure 6:
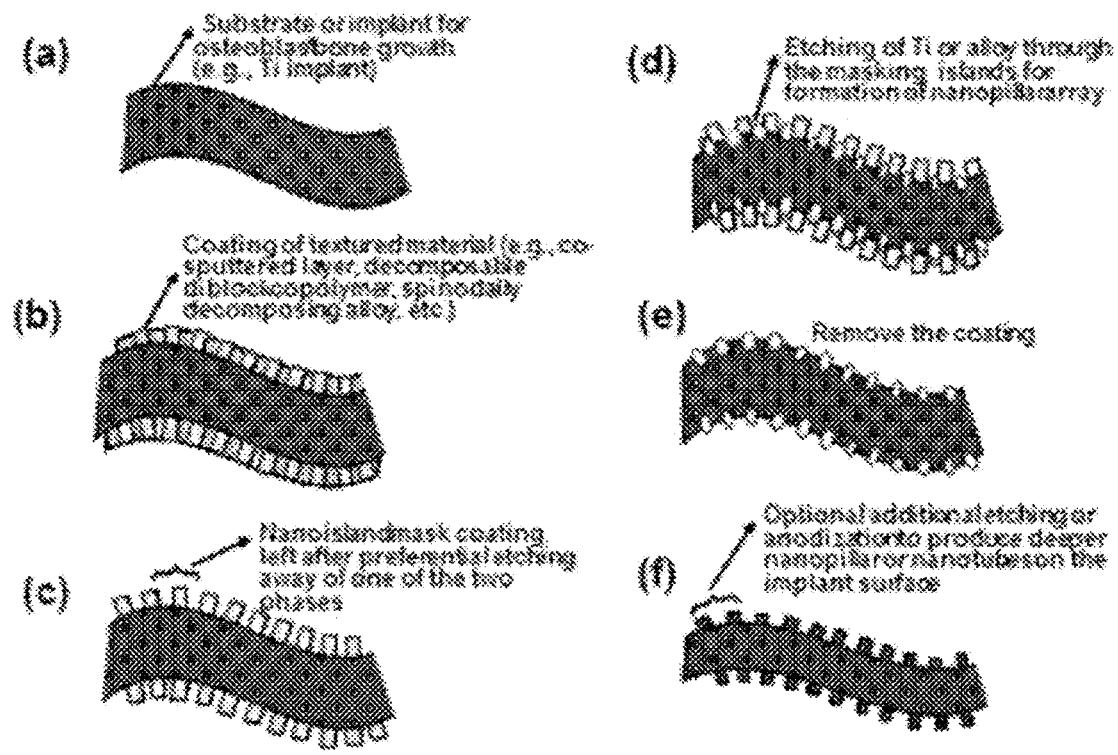
FIG. 6(a)-(f): schematically illustrate a "guided etching" exemplary process for making devices of the invention, where nanopillar arrays on flat or non-flat surfaces by an exemplary "guided etching" process using a vertically two-phase decomposed coating, for example, using a diblock copolymer or a two-phase allow film.

Yet another alternative technique of forming such a desired, location-guided and diameter-guided uniform nanopillar array, especially advantageous for fabricating nanopillar structure on non-flat surface of Ti or related metals and alloys, according to the invention, is to introduce guided etching using a vertically two-phase decomposable coating as illustrated in FIG. 6. First, Ti implant or substrate for osteoblast culture and bone growth is coated with a material which is then decomposed into a vertically aligned two-phase structure. An example of such a decomposable material is a diblock copolymer layer which, on heating, can decompose into vertically aligned two phases. See an article by M. Park et al., "Block copolymer lithography: Periodic arrays of $10^{11}$ holes in 1 square centimeter", Science, Vol. 272, page 1401 (1997).

Another example of decomposable material leading to a vertically aligned two-phase structure is a spinodally decomposing alloy. See an article by N. Yasui et al, "Perpendicular recording media using phase-separated AlSi films", Journal of Applied Physics, Vol. 97, page 10N103 (2005). Either during the thin film deposition with self-heating during the RF plasma sputter deposition process or with post-deposition annealin ~100-700° C., a desirable vertically aligned nano pore structure or nano island structure can be obtained from a spinodal alloys in general. In the case of Al—Si alloy films, with proper chemical etching, Al can be selectively etched while Si oxidizes into $SiO_2$ porous membrane or $SiO_2$ island array, thus creating a nanopore or nanopillar structure depending on the relative volume fraction of the two phases.

After such a decomposable coating is added and made to decompose into aligned two phase structure, FIG. 6(b), one of the phases is removed from the two phase structure via differential etching, e.g., by chemical etching or ion etching to exhibit a nano island array FIG. 6(c). Etching of Ti or alloy base through the masking islands produces nanopillar array of FIG. 6(d). After the coating material is removed, FIG. 6(e), optional additional etching or guided anodization process may be utilized to further increase the depth of the nanopillars, FIG. 6(f).

In alternative embodiments, diblock copolymers are used; they are made up of two chemically different polymer chains or blocks while they are joined by a covalent bond. Because of this connectivity constraint yet chemical incompatibility with each other, the diblock copolymers tend to phase separate and self-assemble into an ordered (often with a hexagonal geometry), nanoscale, mixed-phase composites. Depending on the chemistry and decomposition conditions, they can form an ordered array with one of the polymer components taking a nano-cylinder shape embedded in the other polymer component. Examples of diblock copolymers include a mixture of polystyrene-polybutadiene and that of polystyrene-polyisoprene. The diblock copolymers are diluted with a solvent such as toluene, and can be dip coated, brush coated or spray coated on a substrate. When the heat is applied and drying proceeds and the copolymer concentration and temperature reaches a critical point, the phase decomposition of the diblock copolymer into an ordered structure takes place. In alternative embodiments, a desired temperature rise to nucleate and grow the ordered decomposed diblock copolymer structure is in the range of between about 50-350° C., or between about 100-250° C.

In alternative embodiments, spinodal alloys are used; they can be spontaneously decomposed into a uniform two phase structure by heating to a high temperature within the spinodal phase stability range. Fe—Cr—Co, Al—Ni—Co—Fe, Cu—Ni—Fe, Cu—Ni—Co, and Al—Si alloys are well known examples of spinodally decomposing alloys. Due to the difference in chemical etchability between the two decomposed phases, a nanoisland mask structure of FIG. 6(c) can be obtained over a large area.

As described in FIG. 6(b), nanostructure patterning on Ti implant surface can utilize diblock copolymer two phase decomposition or spinodal decomposition into two phases, from which one of the phases can be dissolved or etched away (wet etching or dry etching such as reactive ion etch) to leave only one phase nanostructure left, either as an island array or as a porous film layer. These left-over material of diblock copolymer of spinodally decomposed alloy can then be used as a mask to etch (wet or dry) the Ti implant surface to create the desired nanostructure surface pattern.

Another exemplary approach is to use a colloidal material comprising a surfactant type polymer matrix and inorganic nanoparticles, which self-assembles into a periodic array of nanoparticles as the solvent dries up. The self-assembly can be caused by the organic surfactant material such as trioctylphosphine oxide or oleic acid, and the nanoparticles such as quantum dots or magnetic nanoparticles dispersed in the surfactant material are geometrically constrained by the surfactant molecules so as to produce a periodic array of nanoparticles within the surfactant matrix. Colloidal nanoparticle array structures can be incorporated into compositions of the invention as described e.g., by: Sun, et al. Science, Vol. 287, page 1989 (2000); Murray et al., Science, vol. 270, page 1335 (1995).

In alternative embodiments, the dimension of the ordered nano pores in diblock copolymer is on the order of about 10 nm to about 100 nm. Example diblock copolymers include polystyrene (PS)-Poly(b-methyl methacrylate-polystyrene) (PMMA), polystyrene-polybutadiene (PS-PB) and PS-polyisoprene (PI). Any process for the use of an ordered block copolymer structure for nano-island or nanopattern formation can be used, as described e.g., by Park, et al., Science, Vol. 276, page 1402 (1997); Templin et al, Science, Vol. 278, page 1795 (1997); Albrecht et al, Science, Vol. 290, page 2126 (2000); Pai et al, Science, Vol. 303, page 507 (2004); Chan et al, Science, Vol. 286, page 1716 (1999).

In alternative embodiments, a spinodal decomposition is used, e.g., as a two phase decomposition of alloy by a thermodynamic driving force on cooling from a high temperature to a lower temperature. In alternative embodiments, the spinodal decomposition is a convenient way of obtaining relatively uniform and periodic nanostructures. In spinodal alloy compositions, any small or large compositional fluctuation lowers the free energy of the alloy system. See, e.g., an article by J. Cahn, Acta Met, vol. 10, p. 179 (1962), a book by P. G. Shewmon, *Transformations in Metals*, McGraw-Hill Book Company, New York, 1969, page 292-295, and a book by A. G. Guy and J. J. Hren, *Elements of Physical Metallurgy*, Addison-Wesley, Menro Park, Calif., 1974, page 425-427. In alternative embodiments, this uniformity and small particle size is beneficial for use as a nanoscale etch mask to pattern the material layer such as a Ti implant metal or alloy surface.

In alternative embodiments, the after one of the two spinodally decomposed phase is wet etched or dry etched, the remaining phase serving as a nano mask allows the etch patterning of the surface underneath by either wet or dry etching. The nano mask dimension obtained from spinodal decomposition can be small, e.g., in the range of 10-200 nm. Example alloy systems suitable for use for spinodal decomposition include Fe—Cr systems with a composition in the spinodal range (e.g., about.35-65 weight % Cr), Fe—Cr—Co (20-65% Cr, 1-30% Co, and balance Fe), Cu—Ni—Fe (about 15-40% Ni, 15-30% Fe, and balance Cu), Cu—Ni—Co (about.20-40% Ni, 20-40% Co, and balance Cu), Au—Ni (about 20-80% Ni). There are other spinodal alloys which can also be utilized for this invention, such as AlNiCo magnet alloys (Fe—Al—Ni—Co alloys), Cu—Ni—Sn alloys, Cu—Ni—Ru, Al—Zn, Al—Si alloys, and others. An alloy film is first deposited on the material surface to be nano-patterned, for example, on Ti implant. The film deposition can be carried out using well known deposition techniques such as physical vapor deposition (e.g., DC sputtering, RF sputtering, ion beam deposition, thermal or electron-beam evaporation) or chemical deposition (e.g., chemical vapor deposition, electrodeposition, electroless deposition).

In the following example of the invention, the $TiO_2$ nanotubes with 100 nm diameter were fabricated and sputter coated with a thin film of Ta. The enhanced osteoblast cell functionality and accelerated bone matrix formation were demonstrated.

Fabrication of Nanotube Array Structure for Osteoblast Culture Experiments.

Figure 2:
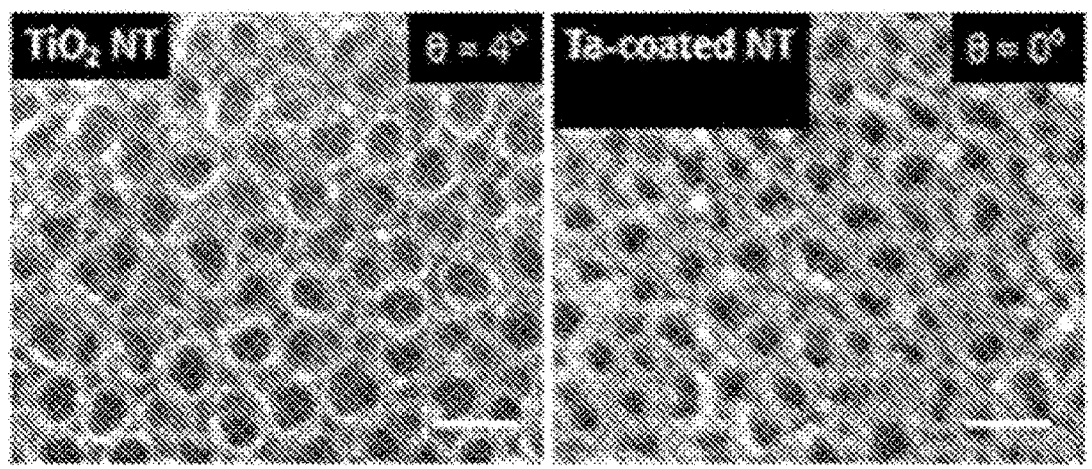
FIG. 2 illustrates two scanning electron microscope (SEM) images of the nanotube substrates. The images depict preservation of the nanotube geometry and structure after tantalum coating. The contact angle for each surface is shown in yellow, indicating an increase in hydrophilicity on the tantalum-coated surface from 4° to 0°. Scale bars=200 nm.

FIG. 2 presents SEM images of both as-made $TiO_2$ nanotube and Ta-coated nanotube surfaces, revealing near identical structures, with an outer diameter of approximately 100 nm, approximately 10 nm wall thickness, approximately 10 nm spacing, and approximately 300 nm height, as previously described, e.g., in references 16 and 17, below. The Ta coating performed by vacuum sputter deposition allows for deposition of a conformal layer with high control of the Ta thickness (20 nm). Ta is a biocompatible material, its corrosion resistance equivalent to Ti, and both Ta and Ta oxide possess low solubility and toxicity, as described in reference 10, below [19]. The Ta coating induced a very slight increase in hydrophilicity from approximately 4° to approximately 0° on the $TiO_2$ and Ta coated surfaces, respectively. Since both remain within the superhydrophilic range, such a slight change in surface energy is not expected to significantly influence cell behavior.

$TiO_2$ nanotube surfaces were created using a two electrode set-up anodization process as described previously e.g., in reference 16, below. A 0.25 mm thick commercially pure Ti sheet (99.5% metal basis, Alfa-Aesar, USA) was used for this process, which was first cleaned successively in acetone and isopropyl alcohol with ultrasonication followed by DI water rinse. The nanotubes were prepared in a 1:7 volumetric ratio of acetic acid (≥99.99% purity, Sigma-Aldrich, USA) to a weight percent fraction of 0.5% hydrofluoric acid in water (48% w/v, EM Science, USA) at 20 V for 30 min. A platinum electrode (99.9%, Alfa-Aesar, USA) served as the cathode. The samples were then washed with deionized water, dried at 80° C., and heat treated at 500° C. for 2 h in order to crystallize the as-fabricated amorphous structured $TiO_2$ nanotubes to anatase structure. Tantalum films (20 nm-thick) were vacuum-deposited onto $TiO_2$ nanotube and flat Ti control substrates from a tantalum target in a Denton Discovery 18 sputter system. To ensure preferential coating of the $TiO_2$ nanotube surface, the deposition angle used was ~30° off the vertical axis with substrate rotation during deposition. 200 W plasma was applied when Ar pressure reached 3 mTorr after base pressure reached $10^{-6}$ torr. The as-deposited Ta film is expected to be of amorphous nature.

Osteoblast Cell Viability and Morphology

Figure 7:
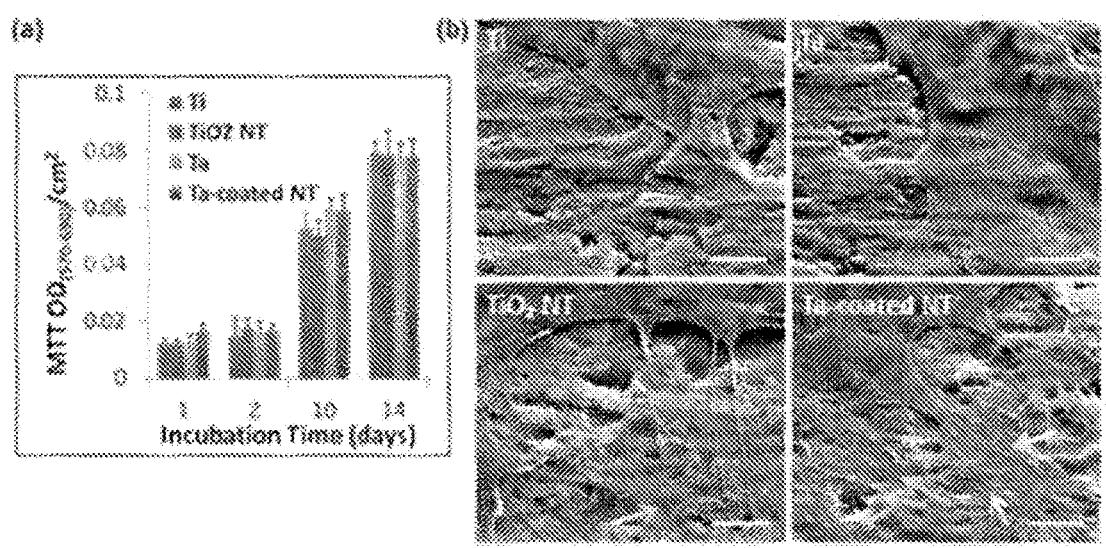
FIG. 7(a) graphically illustrates data from an MTT (3-(4, 5-dimethylthiazole-2-yl)-2,5-diphenyl tetrazolium bromide) assay showing the optical density (OD) of the reaction product of the MTT working solution of human osteoblast (Hob) cells cultured on exemplary nanotube surfaces (Ti, $TiO_2$ nanotubes (NT), Ta, and Ta-coated nanotubes (NT)) as a function of incubation time (n=3); the bar graph shows the mean±standard error bars.
FIG. 7(b) illustrates SEM micrographs of HOb cells after 24 h incubation on the exemplary nanotube surfaces (Ti, $TiO_2$ nanotubes (NT), Ta, and Ta-coated nanotubes (NT)), showing extensive filopodia activity on both nanosurfaces (see arrows); Scale bars=5 µm.

An MTT (3-(4,5-dimethylthiazole-2-yl)-2,5-diphenyl tetrazolium bromide) assay was utilized in order to measure the metabolic activity of the cells and to indirectly estimate the number of viable cells. Results of the MTT analysis in FIG. 7(*a*) show little difference between the flat control samples and the $TiO_2$ and Ta-coated nanotube surfaces. It is likely that the cell adhesion and proliferation is not influenced by the chemistry of the nanotubes. In addition, SEM morphological examination (FIG. 7(*b*)) after 24 h of culture reveals extensive filopodial activity on both $TiO_2$ and Ta surfaces, but not on the flat control surfaces. A common speculation is that finger-like filopodia are a cell-sensing mechanism which are used to detect both chemical and nanotopographical cues, as described e.g., in reference 20, below. An increase in filopodial activity has been demonstrated previously on both $TiO_2$ and $ZrO_2$ nanotube architectures (as described e.g., in references 17 and 21, respectively, below) when compared to respective flat controls surfaces. The presence of many filopodia on both nanotube surfaces indicates that the HOb cells are relatively equally activated by the nanotube architecture, independent of surface chemistry. These results are in agreement with prior results which showed no difference between proliferation, attachment, or morphology between human osteoblast cells cultured on Ta and Ti substrates, as described e.g., in reference 14, below.

Functional Inspection: Bone-Forming Ability

Figure 8:
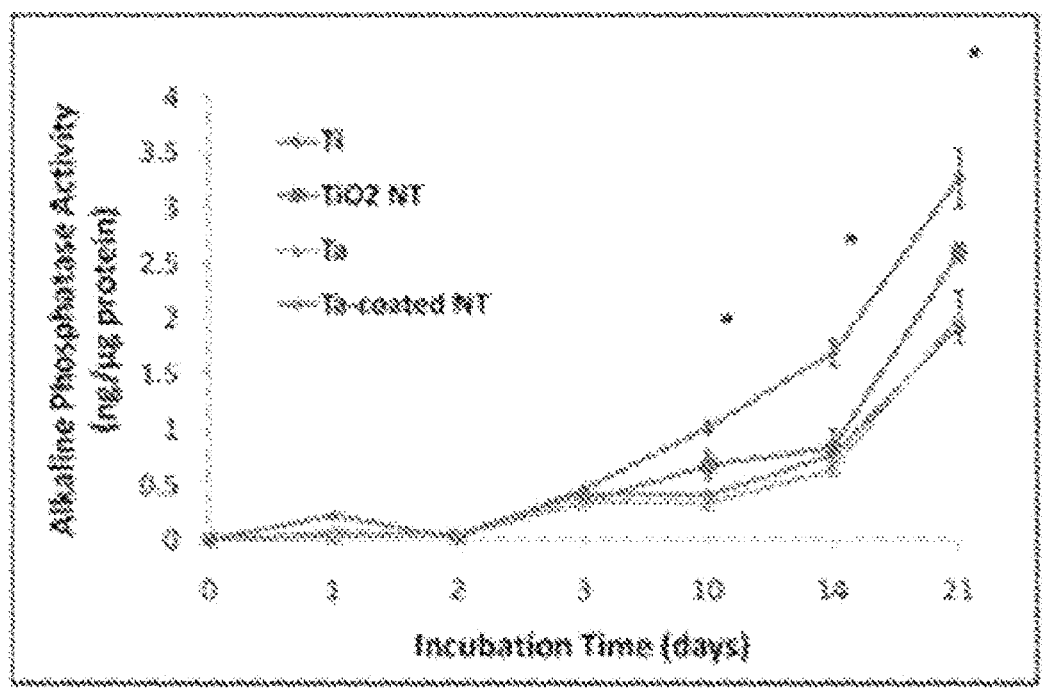
FIG. 8 graphically illustrates data from an Alkaline Phosphatase (ALP) activity of human osteoblast (Hob) cells cultured on the nanotube surfaces (Ti, $TiO_2$ nanotubes (NT), Ta, and Ta-coated nanotubes (NT)) vs. incubation time in days (n=3); the graph points show the mean±standard error bars; the p-values after performing an ANOVA test reaching statistical significance (p<0.001) are marked on the graph (*).

Alkaline phosphatase (ALP) activity was measured as a function of incubation time to estimate the bone-forming ability of osteoblast cells on the experimental substrates (FIG. 8). No difference was observed at shorter time points; however at 10 days and beyond, a significantly higher ALP activity was detected on the Ta-coated nanotube surfaces when compared to all of the other samples. The observed upregulation of ALP activity indicates that the Ta coating may enhance the osteogenic functionality of the HOb cells on the nanotube surface. This trend of increased ALP activity on Ta was also observed by Stiehler, et al., who presented a comparative study of MSC osteogenic response to flat Ti and Ta thin film surfaces deposited on glass discs, as described e.g., in reference 19, below. Since the same trend was observed in a comparison of two films deposited by the same method, one can speculate that the cell behavior was influenced solely by the chemical properties of the elemental surfaces, and not any other surface characteristics. In FIG. 8, one can see a slight increase in ALP activity on the flat Ta control when compared to the flat Ti. However, the Ta-coated nanotube surface is significantly higher in ALP activity than the $TiO_2$ nanotube surface as well as flat controls. This suggests that the combination of nanotube nanostructure and the tantalum surface chemistry may provide an optimal surface for human osteoblast culture.

Figure 9:
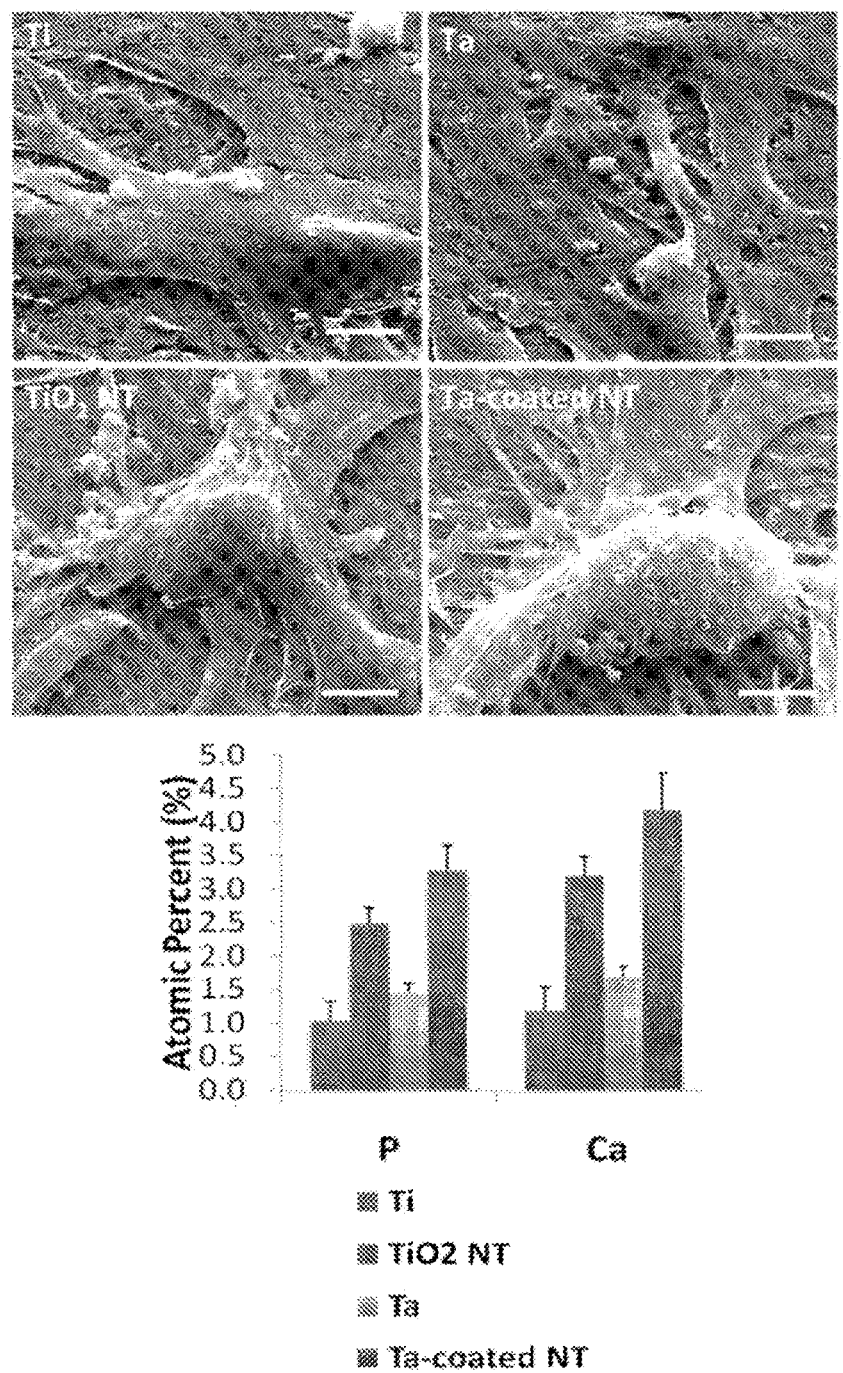
FIG. 9 illustrates bone nodule formation by HOb cells cultured for 3 weeks.

In order to evaluate the degree of matrix mineralization of the bone cells on each experimental surface, the osteoblasts were analyzed for bone nodule formation via various analytical techniques. Bone nodule formation by HOb cells cultured for 3 weeks. FIG. 9(a) SEM micrographs at 1000× showing larger bone nodule formation on the Ta-coated NT surface. Scale bar=20 μm. FIG. 9(b) EDX analysis of the atomic percent of calcium and phosphorous mineral elements on the surfaces (n=5). The bar graph shows the mean±standard error bars. The p-values after performing an ANOVA test reached statistical significance ($p \leq 0.001$), as indicated by (*). After 3 weeks, the presence of large bone nodules was most prominent on the Ta-coated nanotube surface. Furthermore, amounts of P and Ca were significantly higher on the Ta-coated surface However, energy dispersive x-ray (EDX) analysis revealed significantly higher amounts of both phosphorus and calcium (the main components of mineralized bone) on the Ta-coated nanotube samples than was found on all other samples, as shown in the graph in FIG. 9(b). This indicates that although bone nodule formation readily occurred on both nanotube surfaces, the Ta-coating appears to have had the effect of inducing increased deposition of bone matrix minerals. The formation of bone-like apatite on tantalum metal in simulated body fluid has been previously reported, as described e.g., in reference 22, below, as well as on Ti treated with hydrogen peroxide containing tantalum chloride, as described e.g., in reference 23, below. The speculation that the Ta element has apatite-inducing properties supports the hypothesis that it also encourages the production of mineralized matrix by HOb cells.

Figure 10:
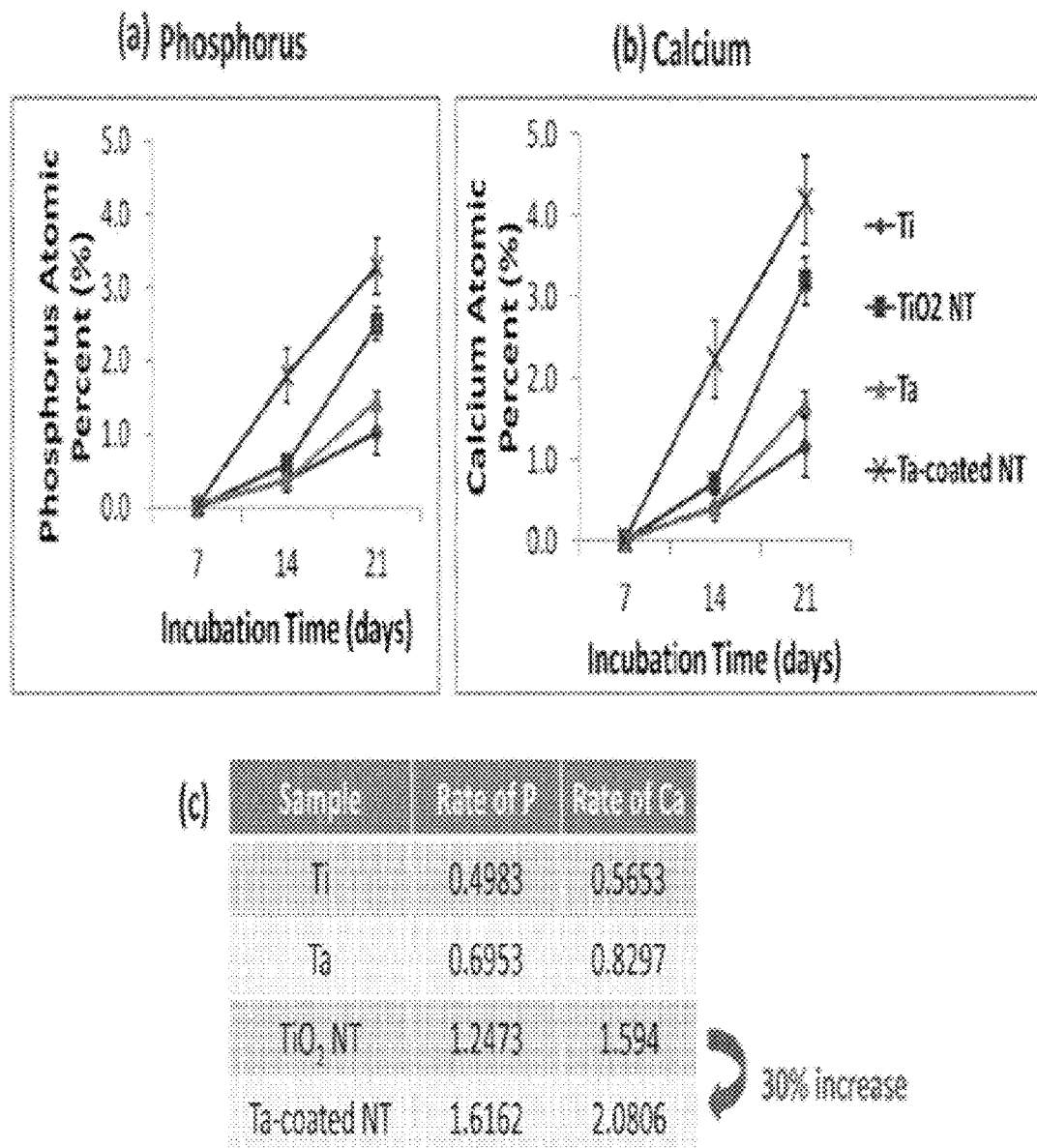
FIG. 10 graphically illustrates Mineralization kinetics studies, an energy dispersive x-ray (EDX) analysis of the atomic percent of phosphorus FIG. 10(a), and calcium FIG. 10(b) mineral elements on the surfaces as a function of time (n=5), with linear trendlines overlaid and correlation coefficients labeled.

The kinetics of matrix mineralization was also examined in order to determine whether the rate of mineralization was affected by the nanostructure or surface chemistry. EDX analysis estimating the atomic percent of phosphorus (FIG. 10(a)) and calcium (FIG. 10(b)) on each substrate after 7, 14, and 21 d of culture revealed that the highest rate of mineralization occurred on the Ta-coated nanotube surface. A linear trendline was estimated for the mineral atomic percent as a function of incubation time for each sample type, and the slope of each line was determined and recorded as the rate of phosphorus or calcium deposition (FIG. 10(c)). It was determined that the rates of both phosphorus and calcium deposition were 30% faster on the Ta-coated nanotube substrate than on the $TiO_2$ nanotube substrate.

Figure 11:
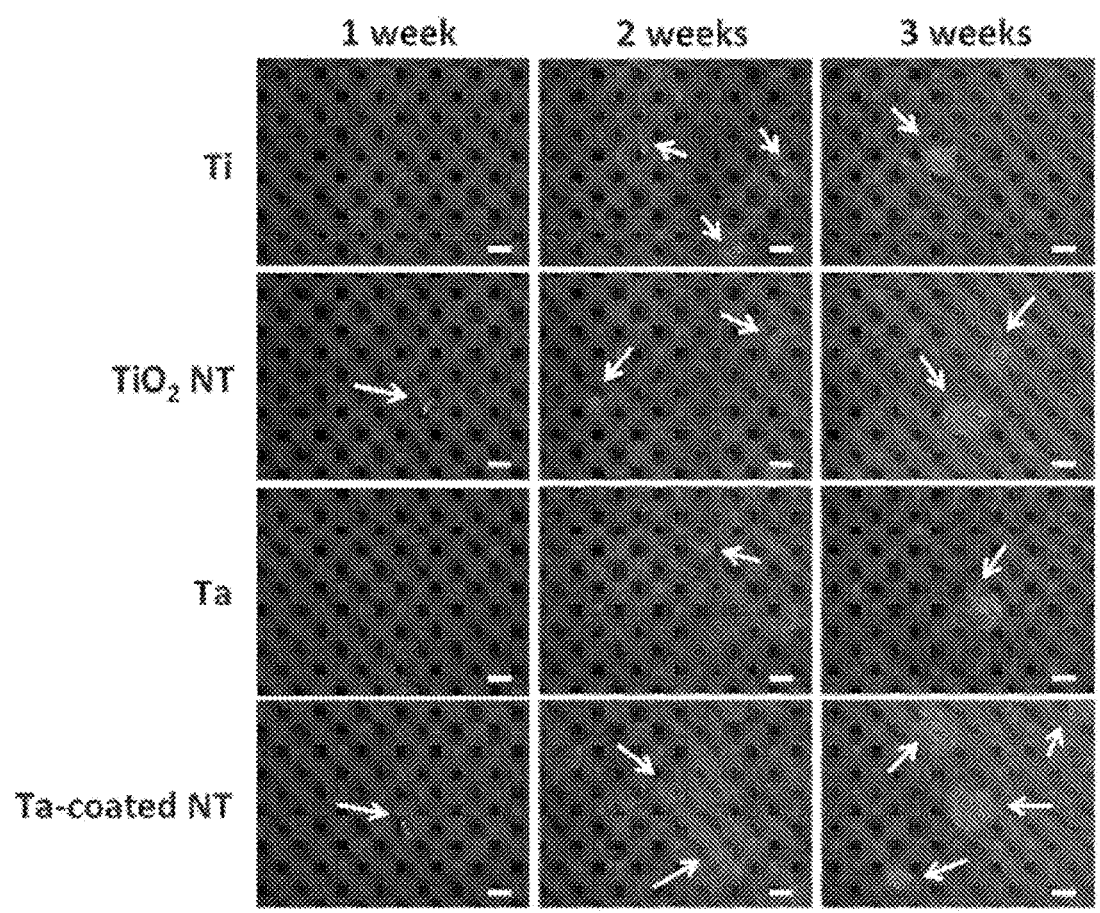
FIG. 11 illustrates alizarin red staining for mineral deposition by HObs cultured for 1, 2, and 3 weeks on the nanotube surfaces (Ti, TiO$_2$ nanotubes (NT), Ta, and Ta-coated nanotubes (NT)); fluorescent images show alizarin red staining (bright red) for mineral deposition; arrows indicate bone nodule formation; Scale bar=50 µm; the results of matrix mineralization kinetics were verified by alizarin red S staining (bright red) at 1, 2, and 3 weeks. The nanotube surfaces appear visually brighter, indicating a higher concentration of Ca deposits.

The results of matrix mineralization kinetics at each incubation time point were verified by alizarin red S staining, a simple and convenient method for detecting calcium mineral deposition. The immunofluorescent images show the stained area (bright red) on each experimental surface after 1, 2, and 3 weeks of culture in FIG. 11 (from left to right). After 1 week, only small amounts of mineral were detected on the $TiO_2$ and Ta-coated nanotube surfaces, while nothing was visible on the flat substrates. After 2 weeks, more highly concentrated areas of calcium mineral deposits (indicated by arrows) were visible on the nanotube surfaces. After 3 weeks, large areas of bone nodules were present on the nanotube surfaces. The amount of large nodules present on the Ta-coated nanotube surface also appears to be the greatest. These results are a visual verification of the observations by EDX analysis. In addition, increased alizarin red staining was reported by Stiehler, et al. (see reference 19, below) of MSCs on Ta when compared to Ti, which confirms the results of this invention, as described herein.

Both the $TiO_2$ and Ta-coated nanotube surfaces enhanced osteoblast growth and function over that of flat controls of smooth Ti and Ta-coated smooth Ti. However, the Ta-coated nanotube surfaces had superior osteofunctionality in terms of ALP activity, bone nodule formation, and the rate of matrix mineralization. These results indicate that although HOb spreading, proliferation, and morphology are influenced primarily by nanotopographical cues, the osteogenesis may be more highly influenced by surface chemistry/material properties than nanotopography. This hypothesis agrees with the previous findings on carbon-coated nanotube surfaces, see e.g., reference 24, below. While the interplay of these surface characteristics are not completely understood, it is apparent that unique combinations can have substantial results. The overall findings of this invention show increased osteogenic response on Ta-coated nanotubes, indicating that the surface chemistry associated with metallic Ta, and thus the compositions of this invention, provide a substantial opportunity for creating the optimal bone implant surface.

In alternative embodiments, a purpose of this invention is to enhance the osteoblast response to Ta versus $TiO_2$ nanotube surfaces in terms of bone-forming ability. The results of this invention demonstrate that nanotopographical Ta triggers enhanced osteofunctionality and matrix mineralization from adult human osteoblast cells. While the differences in the observed osteoblast response to the $TiO_2$ and Ta nanotube surfaces are apparent, it cannot be concluded whether it is a result of solely the surface chemistries. With the addition of the Ta coating, it was observed that a slight change in hydrophilicity, occurs as compared to the anatase crystalline surface of the $TiO_2$ nanotubes. One embodiment of the invention is that the nanodepot space within the nanotubes or in the space between the nanopillars can be utilized to conveniently store biological agents desirable for enhanced culture of chondrocytes, like a growth factor, other biomolecules, antibiotics, etc. which can be slowly released from the $TiO_2$ nanotubes, coated with a Ta or Ta oxide surface layer. The nanoscale space of the $TiO_2$ nanotubes or spacing between the nanopillars, as compared to microsized pores, has an advantage of being able to keep the stored biological agents much longer and allow slower release over a longer period of time. Controlled slow release of drugs such as antibiotics (such as penicillin, streptomycin, vancomycin) can prevent infections near the bone implant. Growth factors stored and slowly released from the nanodepot space can also enhance osteoblast growth and maturation over extended period of time.

In alternative embodiments, the biological agents that can conveniently be stored in such nanodepot space include growth factors, collagens, various proteins/biomolecules, genes, DNAs, antibiotics, hormones, therapeutic drugs, functional particles like magnetic, metallic, ceramic, polymer particles. The functional particles made of magnetic oxide particles or metallic particles can be utilized for remotely actuated RF heating and creation of temperature gradient for accelerated or switch-on, switch-off release of the biological agents stored in the nanodepots.

Figure 12:
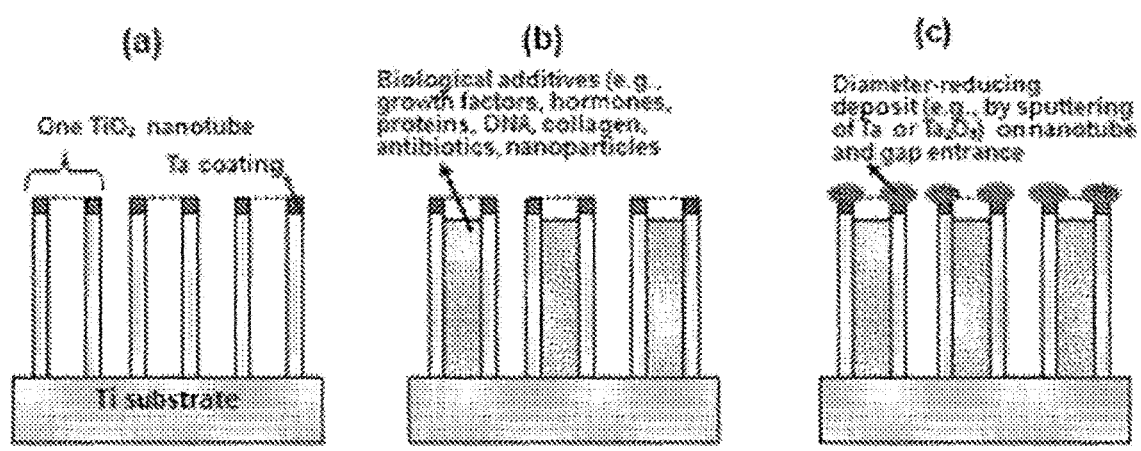
FIG. 12 schematically illustrates exemplary embodiments comprising TiO$_2$ nanotube-based devices, such as e.g., implants, wherein the nanotubes have a Ta or Ta oxide (Ta$_2$O$_5$) coating, alternatively with one or more agents, e.g., biological agents, e.g., slow-releasing biological agents, stored in the vertically aligned nanotube pores.
Figure 13:
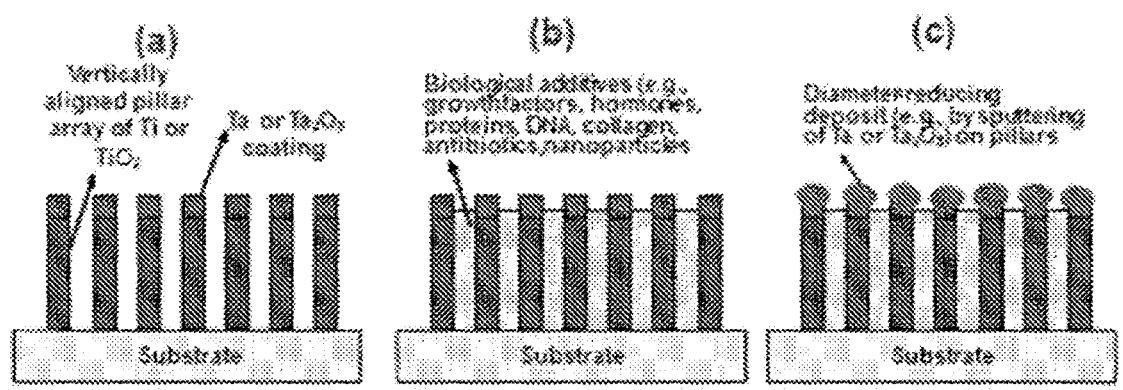
FIG. 13 schematically illustrates exemplary embodiments comprising TiO$_2$ nano-pillar configured implants comprising agents, e.g., biological agents, e.g., slow-releasing biological agents, stored in the gap between the vertically aligned nanopillars.
Figure 14:
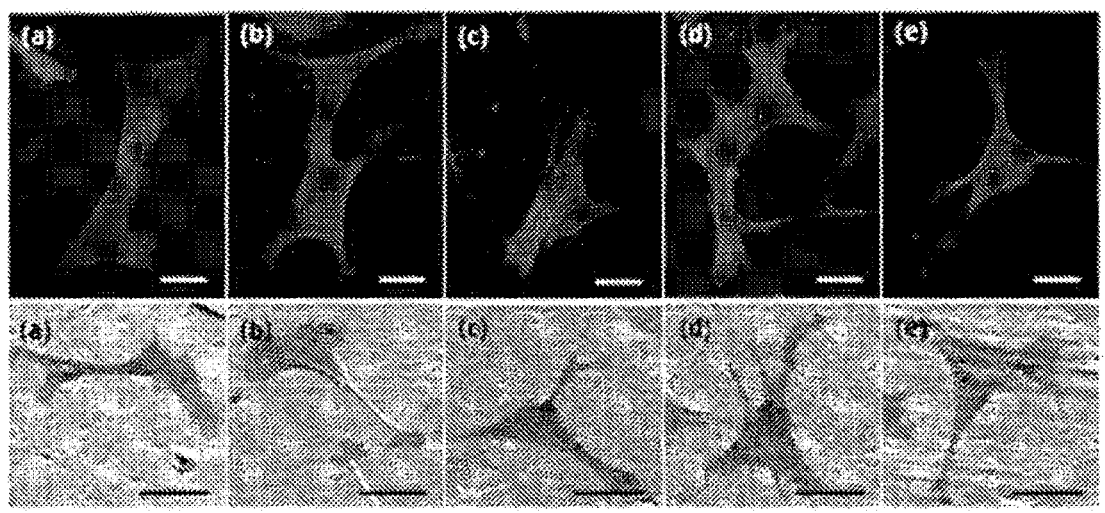
FIG. 14: Top Row: illustrations of Immunofluorescent images of cytoskeletal actin (red) of HOb cells after 24 h of culture incubation, showing a crisscross pattern on both TiO$_2$ and Ta surfaces (yellow arrows) (scale bars=50 µm); and, Bottom Row: illustrations of SEM micrographs of HOb cells after 24 h incubation (scale bars=50 µm)
Figure 15:
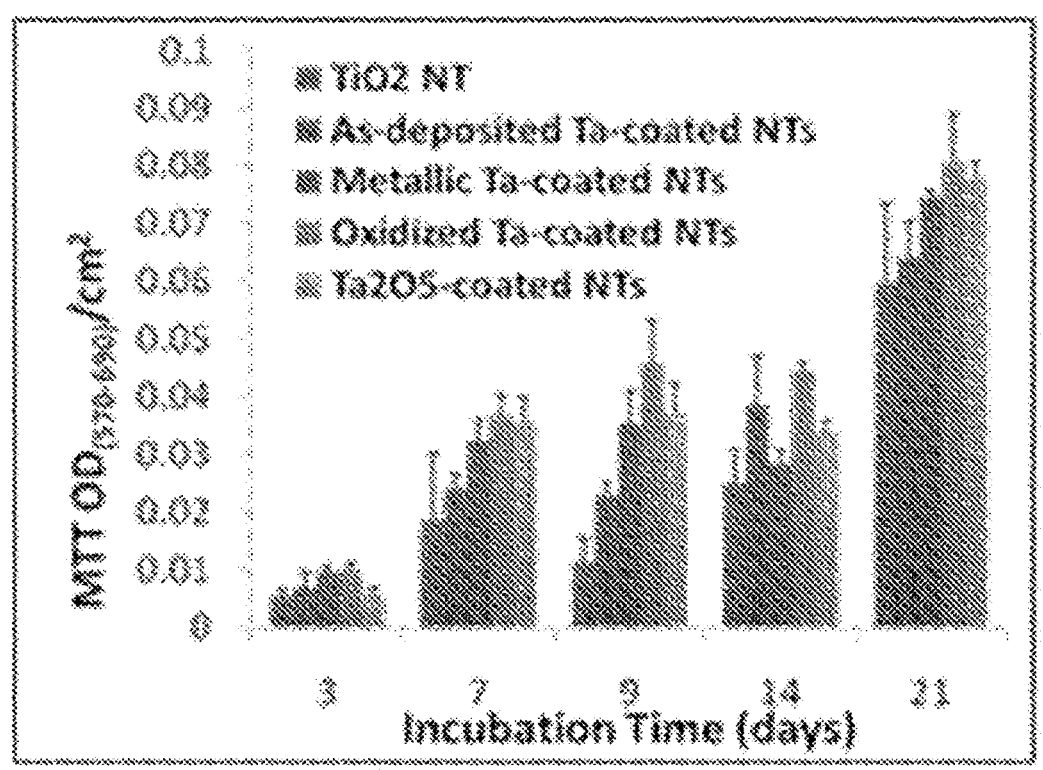
FIG. 15 graphically illustrates data from an MTT assay data showing the optical density (OD) of the reaction product of the MTT working solution of HOb cells cultured on the nanotube (NT) surfaces (TiO$_2$ NTs, as deposited Ta-coated NTs, metallic-coated NTs, oxidized Ta-coated NTs, Ta$_2$O$_5$ surface-coated NTs) as a function of incubation time (n=3); the bar graph shows the mean±standard error bars; wherein the MTT assay shows cell viability, or the estimated live cells on each surface. At 21 days the metallic-coated NTs, oxidized Ta-coated NTs, and Ta$_2$O$_5$ surface-coated NTs show greater "estimated live cell" viability.
Figure 16:
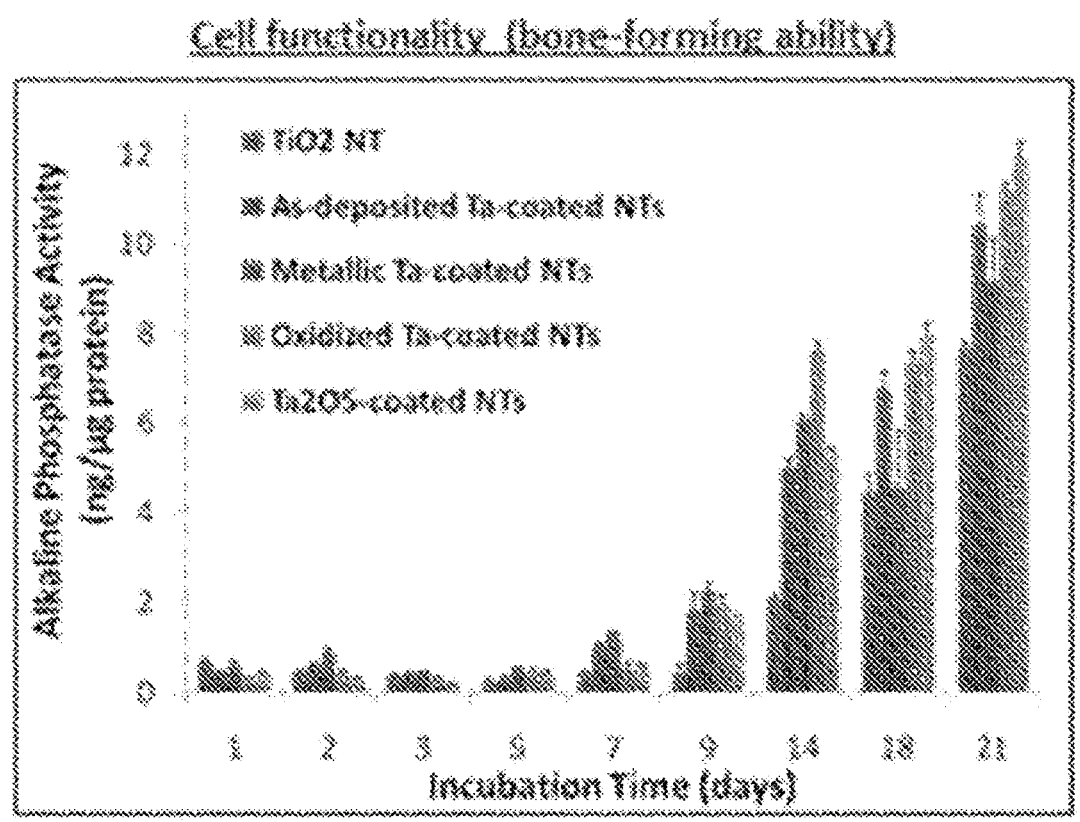
FIG. 16 graphically illustrates data from an Alkaline Phosphatase (ALP) activity (which reflects the cells' functionality, or bone-forming ability) of HOb cells cultured on the nanotube surfaces (TiO$_2$ NTs, as deposited Ta-coated NTs, metallic-coated NTs, oxidized Ta-coated NTs, Ta$_2$O$_5$ surface-coated NTs) vs. incubation time (n=3); the graph points show the mean±standard error bars. The osteoblast cells functionality seems to favor the oxidized tantalum surfaces over the metallic and as-deposited Ta.
Figure 17:
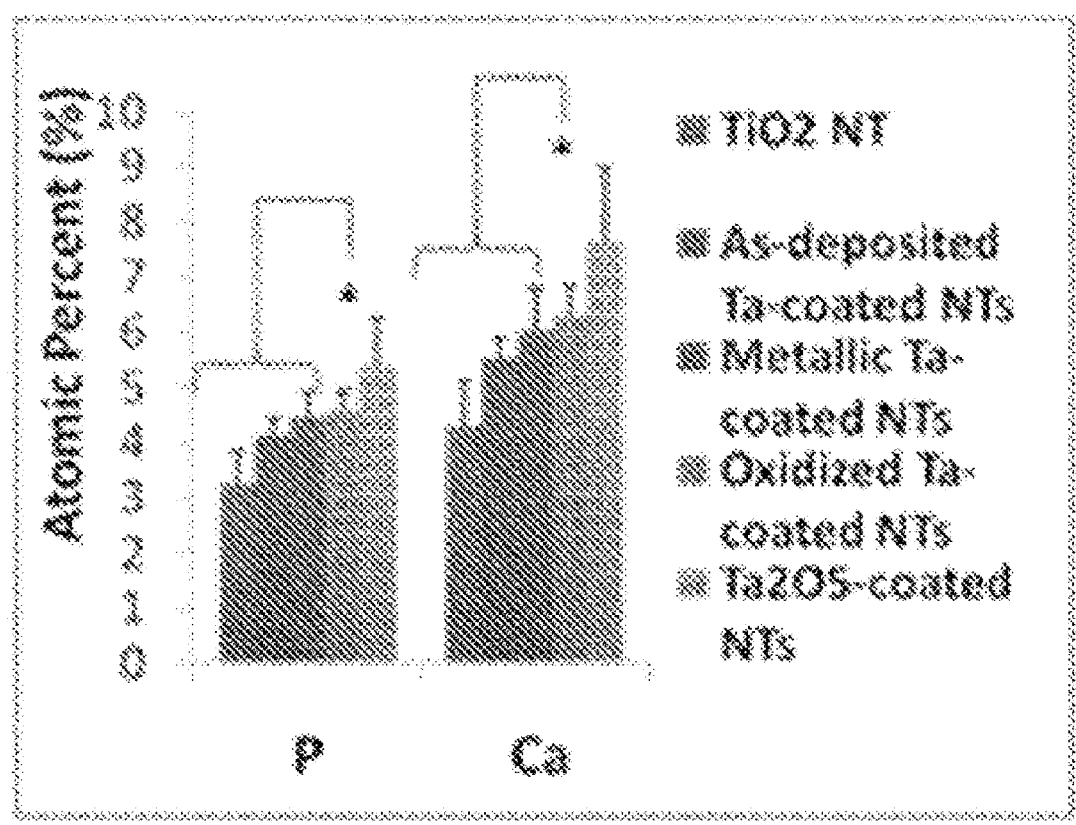
FIG. 17 graphically illustrates data from a bone nodule formation assay (or matrix mineralization, or bone formation) by HOb cells cultured for 3 weeks: (Left graph is for P or phosphorus, and right graph is for Ca or calcium) energy dispersive x-ray (EDX) analysis of the atomic percent of calcium and phosphorous mineral elements on the surfaces (TiO$_2$ NTs, as deposited Ta-coated NTs, metallic-coated NTs, oxidized Ta-coated NTs, Ta$_2$O$_5$ surface-coated NTs) (n=5); the bar graph shows the mean±standard error bars; the p-values after performing an ANOVA test reached statistical significance (p≤0.001), as indicated by (*).
Figure 18:
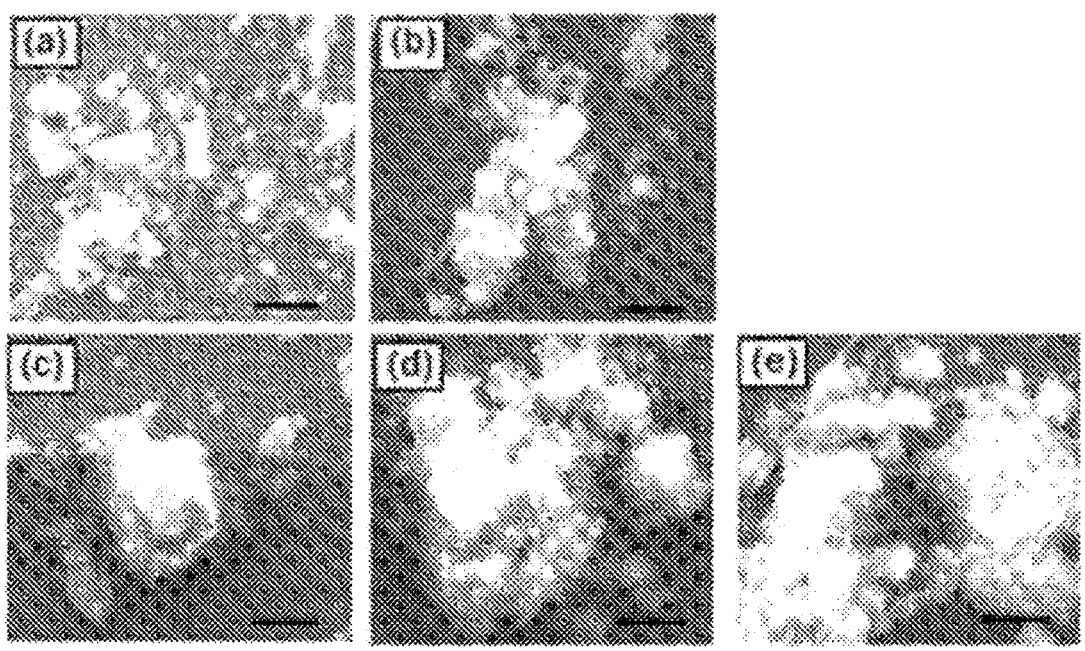
FIG. 18 illustrates SEM micrographs at 2,000× showing the relative degree of bone nodule formation by HOb cells cultured for 3 weeks Larger bone nodule formation is evident on Ta$_2$O$_5$-coated nanotube surface as compared to the Ta metal coated surface. Scale bars=10 µm. (a) TiO$_2$ NTs, (b) as-deposited Ta-coated NTs, (c) metallic Ta-coated NTs (vacuum annealed), (d) oxidized Ta-coated NTs (annealed in air), (e) Ta$_2$O$_5$-coated NTs (directly RF sputtered). The bone mineralization favored the oxidized tantalum surfaces over the metallic and as-deposited Ta.

Referring to the drawings, FIG. 12 schematically illustrates further improved embodiment of $TiO_2$ nanotube based implants comprising nanotubes coated with a Ta surface layer with slow-releasing biological agents stored in the vertically aligned nanotube pores. FIG. 12(a) portrays an array of the as-made $TiO_2$ nanotubes coated with a thin film of Ta, FIG. 12(b) shows the nano array with biological agents stored in the nano-depots. For accelerated bone matrix formation, the TiO$_2$ nanotubes can be made taller, e.g., 1-10 micrometers tall, instead of just 200 to 500 nm tall nanotubes, so that more biological agents can be stored and more slow release for longer period can be accomplished. An alternative inventive approach to slow down the release of the stored biological agents is to make the nanotube entrance narrower by intentional sputtering or evaporation deposition of Ta or $Ta_2O_5$. This is schematically illustrated in FIG. 12(*c*). While regular vertical incident deposition also tends to form such bottle necks, an optional oblique incident deposition with rotating substrate during deposition makes it easier to form the intentional bottle neck configuration.

In alternative embodiments, a nano-depot storage and slow release of the biological agents is accomplished with the nanopillar array structure. This is schematically illustrated in FIG. 13. With the intentionally induced bottleneck configuration, the slow rate release is achieved.

In alternative embodiments, vertically aligned $TiO_2$ and related materials in nanotube or nanopillar array configurations are used, optionally with nano-depot based reservoir and slow release of chemicals or biological agents, which optionally can substantially enhance the kinetics and quantity of osteoblast functionality and mineralized matrix formation, e.g., by at least 30%, or at least 50%, as compared with the same bio implant material or bio substrate material without these nanotube or nanopillar structure.

In alternative embodiments various types of surface nanostructured or microstructured cell-culture or bone-culture substrates are to practice this invention, e.g., they can be used either for in vitro culture of cells and bones, or as a part of in vivo implant structures. Such enhanced bone growth can be useful for a variety therapeutic applications for human and animals. In alternative embodiments methods of the invention provides supportive scaffolding for new bone growth at any bone implant site, including but not limited to:

Finger joint repair or replacement
Wrist repair or replacement
Elbow repair or replacement
Shoulder repair or replacement
Legs
Arms
Hip repair or replacement
Knee repair or replacement
Ankle repair or replacement
Feet and toes repair or replacement
Intervertebral discs of the spinal cord repair or replacement
Rib cage repair or replacement
Any rod, screw or other bone stabilizer implant In alternative embodiments, the invention enables joint or bone repair or replacement while providing the structural support and chemical environment for new bone tissue to grow and fill the defect, and hence can replace damaged, infected, aged, or diseased bone caused by various diseases such as: osteoporosis or an autoimmune disease, e.g. where the immune system attacks the body's cells and tissue, resulting in bone decay or damage.

The types of cells or hard tissues that can be cultured in an enhanced manner by products and methods of the inventive, e.g., the Ta coated substrates, include osteoblast cells, periodontal cells, or stem cells, for the rapid formation/growth of strongly adherent bones. The structures of the invention can be useful for reliable and faster orthopedic or dental bone repair, or for externally controllable drug release and therapeutic treatments.

It is understood that the above-described embodiments are illustrative of only a few of the many possible specific embodiments which can represent applications of the invention. Numerous and varied other arrangements can be made by those skilled in the art without departing from the spirit and scope of the invention.

REFERENCES

[1] Lampin M, Warocquier C, Legris C, Degrange M, Sigot-Luizard M F. Correlation between substratum roughness and wettability, cell adhesion, and cell migration. J Biomed Mater Res 1997; 36:99-108.
[2] Deligianni D D, Katsala N, Ladas S, Sotiropoulou D, Amedee J, Missirlis Y F. Effect of surface roughness of the titanium alloy Ti-6Al-4V on human bone marrow cell response and on protein adsorption. Biomaterials 2001; 22:1241-51.
[3] Deligianni D D, Katsala N D, Koutsoukos P G, Missirlis Y F. Effect of surface roughness of hydroxyapatite on human bone marrow cell adhesion, proliferation, differentiation and detachment strength. Biomaterials 2001; 22:87-96.
[4] Sista S, Wen C, Hodgson P D, Pande G. The influence of surface energy of titanium-zirconium alloy on osteoblast cell functions in vitro. J Biomed Mater Res A 2011.
[5] Dalby M J. Topographically induced direct cell mechanotransduction. Med Eng Phys 2005; 27:730-42.
[6] Dalby M J. Cellular response to low adhesion nanotopographies. Int J Nanomedicine 2007; 2:373-81.
[7] Dalby M J. Nanostructured surfaces: cell engineering and cell biology. Nanomedicine (Lond) 2009; 4:247-8.
[8] Biggs M J, Richards R G, Gadegaard N, Wilkinson C D, Dalby M J. The effects of nanoscale pits on primary human osteoblast adhesion formation and cellular spreading. J Mater Sci Mater Med 2007; 18:399-404.
[9] Meirelles L, Currie F, Jacobsson M, Albrektsson T, Wennerberg A. The effect of chemical and nanotopographical modifications on the early stages of osseointegration. Int J Oral Maxillofac Implants 2008; 23:641-7.
[10] Black J. Biological performance of tantalum. Clin Mater 1994; 16:167-73.
[11] Kato H, Nakamura T, Nishiguchi S, Matsusue Y, Kobayashi M, Miyazaki T, et al. Bonding of alkali- and heat-treated tantalum implants to bone. J Biomed Mater Res 2000; 53:28-35.
[12] Balla V K, Banerjee S, Bose S, Bandyopadhyay A. Direct laser processing of a tantalum coating on titanium for bone replacement structures. Acta Biomater 2010; 6:2329-34.
[13] Schildhauer T A, Robie B, Muhr G, Koller M. Bacterial adherence to tantalum versus commonly used orthopedic metallic implant materials. J Orthop Trauma 2006; 20:476-84.
[14] Findlay D M, Welldon K, Atkins G J, Howie D W, Zannettino A C, Bobyn D. The proliferation and phenotypic expression of human osteoblasts on tantalum metal. Biomaterials 2004; 25:2215-27.
[15] Sagomonyants K B, Hakim-Zargar M, Jhaveri A, Aronow M S, Gronowicz G. Porous tantalum stimulates the proliferation and osteogenesis of osteoblasts from elderly female patients. J Orthop Res 2011; 29:609-16.
[16] Oh S, Daraio C, Chen L H, Pisanic T R, Finones R R, Jin S. Significantly accelerated osteoblast cell growth on aligned TiO2 nanotubes. J Biomed Mater Res A 2006; 78:97-103.

[17] Brammer K S, Oh S, Cobb C J, Bjursten L M, van der Heyde H, Jin S. Improved bone-forming functionality on diameter-controlled TiO(2) nanotube surface. Acta Biomater 2009; 5:3215-23.
[18] Oh S, Brammer K S, Li Y S, Teng D, Engler A J, Chien S, et al. Stem cell fate dictated solely by altered nanotube dimension. Proc Natl Acad Sci USA 2009; 106:2130-5.
[19] Stiehler M, Lind M, Mygind T, Baatrup A, Dolatshahi-Pirouz A, Li H, et al. Morphology, proliferation, and osteogenic differentiation of mesenchymal stem cells cultured on titanium, tantalum, and chromium surfaces. J Biomed Mater Res A 2008; 86:448-58.
[20] Dalby M J, Riehle M O, Johnstone H, Affrossman S, Curtis A S. Investigating the limits of filopodial sensing: a brief report using SEM to image the interaction between 10 nm high nano-topography and fibroblast filopodia. Cell Biol Int 2004; 28:229-36.
[21] Frandsen C J, Brammer K S, Noh K, Connelly L S, Oh S, Chen L H, et al. Zirconium oxide nanotube surface prompts increased osteoblast functionality and mineralization. Mat Sci Eng C-Mater 2011; 31:1716-22.
[22] Miyazaki T, Kim H M, Kokubo T, Kato H, Nakamura T. Induction and acceleration of bonelike apatite formation on tantalum oxide gel in simulated body fluid. J Sol-Gel Sci Techn 2001; 21:83-8.
[23] Kaneko S, Tsuru K, Hayakawa S, Takemoto S, Ohtsuki C, Ozaki T, et al. In vivo evaluation of bone-bonding of titanium metal chemically treated with a hydrogen peroxide solution containing tantalum chloride. Biomaterials 2001; 22:875-81.
[24] Brammer K S, Choi C, Frandsen C J, Oh S, Johnston G, Jin S. Comparative cell behavior on carbon-coated TiO2 nanotube surfaces for osteoblasts vs. osteo-progenitor cells. Acta Biomater 2011; 7:2697-703.

The invention will be further described with reference to the following examples; however, it is to be understood that the invention is not limited to such examples.

EXAMPLES

Example 1: Compositions of the Invention are Effective for Inducing Bone Growth

The data presented herein demonstrates compositions of the invention, e.g., comprising biomaterials with Ta or Ta oxide type nanostructures, and methods of the invention, are effective for and can enable accelerated bone growth and can be useful for a variety of uses including rapid and secure orthopedic, dental, periodontal, cell/organ implants, therapeutics, and disease diagnostics. This example also describe making exemplary compositions of the invention.

In alternative embodiments, surfaces of the substrate biomaterials comprise or consist of a Ta or a Ta oxide, or an alloy containing a Ta or Ta oxide. In alternative embodiments other materials are used in the underlying substrate.

In alternative embodiments, products (articles) of manufacture of the invention can enhance osteoblast cell functionality and bone mineral growth by comprising tantalum or tantalum oxide ($Ta_2O_5$) coatings. In alternative embodiments, products (articles) of manufacture of the invention comprise nanostructures (e.g., nanotubes, nanowires) made of Ti or $TiO_2$, or equivalent structures made of other materials but coated with a biocompatible Ta or $Ta_2O_5$ film.

Exemplary nanostructures comprising the Ta surface chemistries enable an enhanced osteoblast mineralization rate and demonstrated bone forming ability at shorter time points.

Referring to the drawings, FIG. 1(a) schematically illustrates exemplary devices comprising self-organized $TiO_2$ based nanotube arrays grown on titanium metal or alloy substrate which are then deposited with a thin film of tantalum (Ta) or Ta oxide ($Ta_2O_5$) by sputter deposition, or ion beam deposition, evaporation, laser ablation, chemical vapor deposition, for use in exemplary methods to accelerate osteoblast cell maturation, as illustrated in FIG. 1(b). In alternative embodiments, $TiO_2$ nanotubes or any other biocompatible nanotubes (e.g., $Al_2O_3$, $ZrO_2$, $HfO_2$, $NbO$ or $Nb_2O_5$, $MoO_2$ or $MoO_3$, $VO_2$ or $V_2O_5$, $WO_2$ or $WO_3$) are used with compositions and devices of the invention; and these nanotubes can have dimensions of between about 10 to 1000 nm in diameter, or between about 30 to 300 nm, or between about 60 to 200 nm in diameter.

In alternative embodiments desired heights of the tubules are determined in part by the desired aspect ratio as relatively short height with an aspect ratio of less than 10, preferably less than 5 is preferred for reduced tendency for ease of storing and eventual dispensing of drugs or biological agents intentionally placed within the tubule cavity, as well as to reduce a possibility of long tubules in thick nanotube layers delaminating or breaking off and floating around in the human body. In alternative embodiments a desired height is 40-2000 nm, or 100-600 nm.

In alternative embodiments, instead of or in addition to nanotube shape substrates, nanopillars or nanowires or nanoribbons or equivalent nanostructures are used as the basis (e.g., the superstructure, or template, or surface) to deposit a thin film of Ta (or oxide thereof) to enhance the bone or cartilage formation, or to enhance differentiation of stem cells. In alternative embodiments the desired thickness of Ta coating is in the range of between about 1-1,000 nm, or 5-300 nm, or even more or between about 10-100 nm.

In alternative embodiments a vertical alignment with open top pore is crucial for bio implant and related applications, as the open top of the nanotubes illustrated in FIG. 1(a) allows the penetration of the cells into the nanopore cavity for good adhesion as illustrated in FIG. 1(b). Cells that adhere well to a surface generally remain healthy and grow quickly, while the cells that do not adhere exhibit reduced or minimal growth.

In a vertical nanotube structure of the invention, an example of which is shown in FIG. 2, such a desirable configuration is provided. FIG. 2 also depicts preservation of the nanotube geometry and structure after tantalum coating. The contact angle for each surface is shown in yellow, indicating an increase in hydrophilicity on the tantalum-coated surface from 4° to 0°. In alternative embodiments, the implant comprising Ta coated nanotube or nanowire surface structure for enhanced bone and cartilage growth has improved hydrophilicity in terms of water droplet contact angle of less than 3 degrees, preferably less than 2 degrees.

In alternative embodiments titanium nanotubes are formed by electrolytic anodization, for example using 5% hydrofluoric acid and applying approximately 10-20 volts of potential, and allowing several minutes to a few hours depending on the temperature and other electrochemical process parameters. The resultant $TiO_2$ nanotube diameter is dependent on the anodization voltage.

FIGS. 14 to 18 present data of oxidized tantalum studies to compare metallic Ta coating versus (vs) Ta-oxide coating on surfaces of nanostructures on devices of the invention and their ability to induce or stimulate on human osteoblast cell growth and bone formation). Experiments were on identical types of $TiO_2$ nanotube surface, at approximately 100 nm diameter×approximately 300 nm tall nanotubes by standard anodization process: the various surfaces were: TiO$_2$ nanotubes (as made), Ta-coated nanotubes (as-deposited by sputtering), metallic Ta-coated nanotubes (heat treated in vacuum to provide annealing while keeping it metallic but without Ta-oxide formation), oxidized Ta-coated nanotubes (Ta sputter coated+heat treated in air to convert Ta coating into Ta-oxide coating), and Ta$_2$O$_5$-coated nanotubes (approximately 20 nm thick, directly RF sputter coated from Ta-oxide target at 400 watt power) at approximately 3 milli Torr Ar pressure. From FIGS. 14 to 18, the osteoblast cells functionality and bone mineralization seem to favor the oxidized tantalum surfaces over the metallic and as-deposited Ta.

A number of embodiments of the invention have been described. Nevertheless, it will be understood that various modifications may be made without departing from the spirit and scope of the invention. Accordingly, other embodiments are within the scope of the following claims.

What is claimed is:

1. An implant for inducing or stimulating bone formation in vivo comprising:
    a plurality of Ti or TiO$_2$ comprising nanotubes approximately 100 nm diameter by approximately 300 nm tall on a biocompatible substrate,
    wherein the plurality of nanotubes is covered, coated or layered by a from about 1 to 100 nanometers (nm) thick covering, coating or layer of tantalum B oxide Ta$_2$O$_5$ on at least 25% or more of the surface of the plurality of nanotubes.
2. The implant of claim 1, further comprising or having on its biocompatible substrate surface a microscale structure or a plurality of microscale structures.
3. The implant of claim 1, manufactured as or for use as: a biomedical device, a bone pin, an intramedullary rod, an intramedullary nail (IM nail) or inter-locking nail or Küntscher nail; or a pin, a plate or a post; or an equivalent thereof.
4. The implant of claim 1, further comprising: a cell or a plurality of cells.
5. The implant of claim 1, wherein the biocompatible substrate comprises a member of the group consisting of:
    (a) an alloy comprising a titanium (Ti), a titanium oxide, a TiO$_2$, or a combination thereof;
    (b) an alloy comprising a Ti, a Ti oxide or a combination thereof;
    (c) a metallic component;
    (d) a rare earth element;
    (e) a stainless steel;
    (f) a Si or a Si oxide;
    (g) a carbon or a diamond;
    (h) a ceramic;
    (i) a polymer or a plastic material; and
    (j) a combination thereof.
6. The implant of claim 1, further comprising a chemical, a compound, a small molecule, an agent, an active B agent, a biological agent, a drug or a tracer.
7. The implant of claim 1, wherein the implant is manufactured as or for use as a bone implant.
8. The implant of claim 1, wherein the implant is:
    (a) a bone or a tooth implant, a joint replacement, a bone implant, a bone B onlay, a bone support site, or a bone screw; or
    (b) an orthopaedic, a dental, a spinal, a knee, or a joint implant.
9. The implant of claim 8, wherein the joint replacement, bone implant, bone onlay, bone support site or B bone screw is, or is fabricated for, or is fabricated to replace all or part of:
    a finger joint repair or replacement, a wrist repair or replacement, an elbow repair or replacement, a shoulder repair or replacement, a leg repair or replacement, an arms repair or replacement, a hip repair or replacement, a knee repair or replacement, an ankle repair or replacement, a foot or a toe repair or replacement, an intervertebral disc of a spinal cord repair or replacement, a rib cage repair or a rib B replacement, a skull mesh, patch or replacement, a pin, a mesh or a rod, a screw or a bone stabilizer implant.
10. The implant of claim 1, wherein the plurality of nanotubes are arranged or fabricated as an array of.
11. The implant of claim 4, wherein the cell or cells are selected from the group consisting of: a human cell; a stem cell; a chondrocyte; a fibroblast; an osteoclast; an osteoblast; a cell involved in odontogenesis or a bone formation; a bone cell; a muscle cell; a liver cell; a liver parenchymal cell; an endothelial cell; an adipocyte; a fibroblastic cell; a Kupffer cell; a kidney cell; a blood vessel cell; a skin cell; a periodontal cell; an odontoblast; a dentinoblast; a cementoblast; an enameloblast; an odontogenic ectomesenchymal tissue; and a combination thereof.
12. The implant of claim 4, wherein the cell or cells are adhered to or growing on the surface of the nanostructure or nanoarchitecture.
13. The implant of claim 1, further comprising a bone, a cartilage, or a grown and adhered bone structure.
14. The implant of claim 13, wherein the bone or adhered bone structure comprises an orthopaedic bone, a dental bone, a spinal bone, a human or an animal bone.
15. The implant of claim 13, wherein the bone or cartilage, or grown and adhered bone structure, is on or is in contact with the Ta$_2$O$_5$.
16. The implant of claim 5, wherein the metallic component of the biocompatible substrate is selected from the group consisting of:
    (a) a ZrO$_2$, a HfO$_2$, a NbO, a Nb$_2$O$_5$, a MoO$_2$, a MOO$_3$, a VO$_2$, a V$_2$O$_5$, a WO$_2$, a WO$_3$, an alloy or oxide thereof, or an oxide thereof;
    (b) a Ti, Zr, Hf, Nb, Mo, V or W oxide;
    (c) an Al, an Ag, a C, a F, a Mg, a Ca, a Si, a P, a Mn, a Fe, a Co, a Cu, a Zn, a Pd, an In, a Sn, a Sb, a Re, an Os, an Ir, a Pt, an Au, or a Bi; and
    (d) a combination thereof.
17. The implant of claim 5, wherein metallic component comprises at least 40% or more by weight.
18. The implant of claim 6, wherein:
    (a) the chemical, compound, small molecule, agent, active agent, biological agent, drug or tracer comprises a member of the group consisting of: a peptide, a protein, a polypeptide, an antibody, a nucleic acid, a DNA or an RNA, an miRNA, an siRNA, a gene, a vector, a polysaccharide, a lipid, a growth factor, a cytokine, an antibiotic, a hormone, a therapeutic drug, a functional particle, a magnetic particle, a metallic particle, ceramic particle, a polymer particle and a combination thereof;
    (b) the chemical, compound, small molecule, agent, active agent, biological B agent, drug or tracer is stored in within, between the spaces or adhered on the plurality of TiO or TiO$_2$ comprising nanotubes; or
    (c) the plurality of TiO or TiO$_2$ comprising nanotubes form a plurality of nanodepots by storing the chemical, compound, small molecule, agent, active agent, biological B agent, drug or tracer within between or on the plurality of TiO or TiO$_2$ comprising nanotubes.

19. The implant of claim 1, wherein:
(a) the plurality of TiO or TiO$_2$ comprising nanotubes further comprise partially blocked or constricted, or triggerable or actuable, or partial bottlenecking configuration, openings, to allow the release of a chemical, compound, small molecule, agent, active agent, biological agent, drug or tracer, in a triggerable, actuable, controlled or slow release fashion;
(b) the plurality of TiO or TiO$_2$ comprising nanotubes further comprise an entrance dimension of a nanodepot reduced by selective deposition of metal or oxide material to induce a partial bottlenecking configuration to slow down a release rate of a chemical, a compound, a small molecule, an active agent, a biological agent, a drug or a tracer stored within; or
(c) the plurality of TiO or TiO$_2$ comprising nanotubes further comprise functional particles made of magnetic oxide particles or metallic particles utilized for remotely actuated RF heating and creation of temperature gradient for accelerated or switch-on, switch-off release of the biological agents stored in the nanodepot space.

20. The implant of claim 1, wherein the thickness of the tantalum oxide Ta$_2$O$_5$ covering, coating or layer is from between about 1 to 9 nanometers (nm).

21. The implant of claim 1, wherein the thickness of the tantalum oxide Ta$_2$O$_5$ covering, coating or layer is from between about 1 to 5 nanometers (nm).

22. The implant of claim 1, wherein the thickness of the tantalum oxide Ta$_2$O$_5$ covering, coating or layer is about 20 nanometers (nm).

23. The implant of claim 1, wherein the biocompatible substrate is covered, coated or layered by a tantalum oxide Ta$_2$O$_5$ on about 95% to 99% of its surface.

24. The implant of claim 21, wherein the thickness of the tantalum oxide Ta$_2$O$_5$ covering, coating or layer is from between about 1 to 3 nanometers (nm).

25. The implant of claim 1, wherein the covering, coating or layer of tantalum oxide Ta$_2$O$_5$ covers, coats or layers from between about 97% to 99% of the plurality of TiO or TiO$_2$ comprising nanotubes.

26. The implant of claim 25, wherein the covering, coating or layer of tantalum oxide Ta$_2$O$_5$ covers, coats or layers greater than about 98% of the plurality of TiO or TiO$_2$ comprising nanotubes.

27. The implant of claim 26, wherein the covering, coating or layer of tantalum oxide Ta$_2$O$_5$ covers, coats or layers 99% or more of the plurality of TiO or TiO$_2$ comprising nanotubes.

28. An in vitro, ex vivo or in vivo cell culture substrate or an in vivo implant substrate for: a new or an enhanced cell growth; a new or an enhanced osteoblast, odontoblast, dentinoblast or cementoblast growth; a new or an enhanced bone or cartilage growth; or a new or an enhanced formation of a mineralized matrix,
wherein the culture substrate comprises, or a surface of the substrate comprises a biocompatible substrate,
wherein the biocompatible substrate comprises a plurality of Ti or TiO$_2$ comprising nanotubes approximately 100 nm diameter by approximately 300 nm tall, and the plurality of nanotubes is covered, coated or layered by a from about 1 to 100 nanometers (nm) B thick covering, coating or layer of tantalum oxide Ta$_2$O$_5$ on at least 25% or more of the surface of the plurality of nanotubes.

29. An in vitro, ex vivo or in vivo implant supportive scaffolding for: a new or an enhanced cell growth; a new or an enhanced osteoblast, odontoblast, dentinoblast or cementoblast growth; a new or an enhanced bone or cartilage growth; a new or an enhanced formation of a mineralized matrix, comprising:
a scaffolding surface comprising a biocompatible substrate,
wherein the biocompatible substrate comprises a plurality of Ti or TiO$_2$ comprising nanotubes approximately 100 nm diameter by approximately 300 nm tall, and the plurality of nanotubes is covered, coated or layered by a from about 1 to 100 nanometers (nm) B thick covering, coating or layer of tantalum oxide Ta$_2$O$_5$ on at least 25% or more of the surface of the plurality of nanotubes.

* * * * *